United States Patent
Lattmann et al.

(10) Patent No.: US 6,596,750 B2
(45) Date of Patent: Jul. 22, 2003

(54) SUBSTITUTED 3,5-DIPHENYL-1,2,4-TRIAZOLES AND THEIR USE AS PHARMACEUTICAL METAL CHELATORS

(75) Inventors: René Lattmann, Binningen (CH); Pierre Acklin, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/252,899

(22) Filed: Sep. 23, 2002

(65) Prior Publication Data
US 2003/0069273 A1 Apr. 10, 2003

Related U.S. Application Data

(60) Division of application No. 09/699,765, filed on Oct. 30, 2000, now Pat. No. 6,465,504, which is a continuation-in-part of application No. 09/202,769, filed as application No. PCT/EP97/03315 on Jun. 24, 1997, now abandoned.

(30) Foreign Application Priority Data

Jun. 25, 1996 (CH) ............... 1593/96

(51) Int. Cl.$^7$ ............... A61K 43/653
(52) U.S. Cl. ............ 514/383; 514/235.8; 514/236.2; 514/236.5; 514/253.09; 514/255.05; 514/255.06; 514/256; 514/326; 514/340; 514/381; 514/382; 514/836
(58) Field of Search ............... 514/383, 836, 514/235.8, 236.2, 236.5, 253.09, 255.05, 255.06, 256, 326, 340, 381, 382

(56) References Cited

U.S. PATENT DOCUMENTS 4,528,196 A 7/1985 Pitt .................. 514/533

FOREIGN PATENT DOCUMENTS

| DE | 4320801 | 1/1995 |
| EP | 185401 | 6/1986 |
| EP | 315434 | 5/1989 |
| EP | 480659 | 4/1992 |
| GB | 1018987 | 2/1966 |
| GB | 1528564 | 10/1978 |

OTHER PUBLICATIONS

Bergeron, et al., J.Med. Chem., vol. 34, pp. 2072–2078 (1991).
Bergeron, et al., Blood, vol. 81, No. 8, pp. 2166–2173 (1993).
Bickel, et al., Helv. Chim. Acta, vol. 46, pp. 1385–1389 (1963).
Chemical Abstracts, vol. 60: 9528g (1964).
Brunetti, et al., Helv. Chim. Acta, vol. 55, pp. 1566–1595 1972).
Chemical Abstracts, vol. 77: 10154w (1972).
Brunner K., Ber. dtsch. chem. es., vol. 47, pp. 2671–2680 (1914).
Chemical Abstracts, vol. 9: 210 (1915).
Brunner K., Mh. Chem., vol. 36, pp. 506–534 (1915).
Chemical Abstracts, vol. 9: 3058 (1915).
Einhorn, et al., Liebigs, Ann. Chem., vol. 343, pp. 223–282 (1905).
Kontoghiorghes, G.J., Toxicology Letters, vol. 80, pp. 1–18 (1995).
Ryabukhin, et al., Translation from Khim. Geterot. Soed., vol. 3, pp. 406–410 (1983).
Wagner, et al., Pharmazie, vol. 35, pp. 48–50 (1980).
Chemical Abstracts, vol. 93: 95196a (1980).
Wagner, et al., Z. Chem., vol. 21, pp. 261 (1981).
Chemical Abstracts, vol. 95: 18716e (1981).
Derwent Abstract 95–070280/10 (1995).
Chemical Abstracts, vol. 122: 306557 (1995).
Ryabukhin, et al., Translation from Koord. Khim., vol. 13, No. 7, pp. 869–874 (1987).

*Primary Examiner*—Frederick Krass
(74) *Attorney, Agent, or Firm*—Joseph J. Borovian

(57) ABSTRACT

The use is described of 3,5-diphenyl-1,2,4-triazoles of the formula I

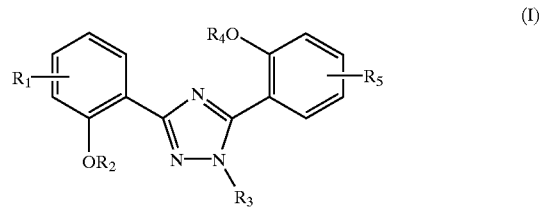

in which $R_1$–$R_5$ are as defined in the description. The compounds have useful pharmaceutical properties and are particularly active as iron chelators. They can be used for the treatment of iron overload in warm-blooded animals.

18 Claims, No Drawings

SUBSTITUTED 3,5-DIPHENYL-1,2,4-TRIAZOLES AND THEIR USE AS PHARMACEUTICAL METAL CHELATORS

This application is a divisional of U.S. application Ser. No. 09/699,765, filed Oct. 30, 2000, now U.S. Pat. No. 6,465,504 which is a continuation-in-part of U.S. application Ser. No. 09/202,769, having a 371 date of Dec. 21, 1998, now abandoned, which is a 371 of International Application No. PCT/EP97/03315, filed Jun. 24, 1997.

Various disorders of warm-blooded animals are linked with an excess of metals, in particular trivalent metals, in the body tissues. For example, aluminum in dialysis encephalopathy and osteomalacia, as well as in Alzheimer's disease is representative. In other illnesses, in particular of man, an excess of iron occurs in the various tissues. This is designated as iron overload (formerly haemosiderosis). It occurs, e.g., after parenteral administration of iron (especially repeated blood transfusions) or after increased uptake of iron from the gastrointestinal tract. Repeated transfusions are necessary in serious anemias, especially in thalassaemia major, the severe form of β-thalassaemia, but also in other anemias. Increased iron absorption from the gastrointestinal tract either takes place primarily, e.g. on account of a genetic defect (so-called haemochromatosis), or secondarily, such as after anemias in which blood transfusions are not necessary, e.g. thalassaemia intermedia, a milder form of β-thalassaemia.

Untreated iron overload can cause severe organ damage, in particular of the liver, the heart and the endocrine organs, and can lead to death. Iron chelators are able to mobilize and excrete the iron deposited in the organs and thus lower the iron-related morbidity and mortality.

A reduction in the iron(III) concentration is also of interest for the treatment of disorders due to iron(III)-dependent microorganisms and parasites, which is of key importance not only in human medicine, such as in particular in malaria, but also in veterinary medicine. Complexing of other metals, in partcular trivalent metals, can also be used for excretion thereof from the organism. A number of further applications are also described in the literature, e.g. by Kontoghiorghes, Toxicology Lett. 80:1–18 (1995).

Desferrioxamine B has already been known for a long time and used therapeutically for these purposes [Bickel et al., Helv. Chim. Acta 46:1385–1389 (1963)]. A disadvantage of this preparation, however, turns out to be the fact that desferrioxamine and its salts only have a low, inadequate activity on oral administration and require a parenteral administration form in all of the abovementioned application possibilities. It is thus recommended, e.g., as a particularly effective method to administer the active substance by means of a slow (8 to 12 hour) subcutaneous infusion, which, however, demands the use of a portable mechanical device, such as an infusion syringe actuated by an electrical drive. Apart from their awkwardness, such solutions are affected by a high treatment cost, which severely restricts their use; in particular a comprehensive treatment of the thalassaemias in the countries of the Mediterranean region, of the Middle East, India and South-East Asia, of malaria worldwide and of sickle-cell anemia in African countries is made impossible. These widespread diseases are furthermore a serious problem for the health service in these countries and make the search for a simpler and more inexpensive therapy, preferably by means of an orally active preparation, the urgent object in this area.

Various 3,5-diphenyl-1,2,4-triazoles have been known for a long time and their use is described for herbicides, e.g. in EP 185,401, as angiotensin II receptor antagonists in EP 480,659, or very generally as intermediates and starting compounds for fine chemicals, e.g. in JP 06345728.

It has now been found that certain substituted 3,5-diphenyl-1,2,4-triazoles have valuable pharmacological properties when used in the treatment of disorders which cause an excess of metal in the human or animal body or are caused by it, primarily a marked binding of trivalent metal ions, in particular those of iron [Martell and Motekaitis, Determination and Use of Stability Constants, VCH Publishers, New York (1992)]. They are able, e.g. in an animal model using the non-iron overloaded cholodocostomized rat [Bergeron et al., J. Med. Chem. 34:2072–2078 (1991)] or the iron-overloaded monkey [Bergeron et al., Blood 81:2166–2173 (1993)] in doses from approximately 5 μmol/kg, inter alia, to prevent the deposition of iron-containing pigments and in the case of existing iron deposits in the body cause excretion of the iron.

The present invention relates to the use of compounds of the formula I

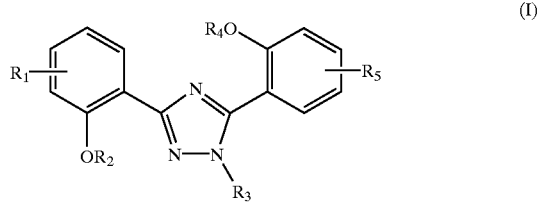

in which
  $R_1$ and $R_5$ simultaneously or independently of one another are hydrogen, halogen, hydroxyl, lower alkyl, halo-lower alkyl, lower alkoxy, halo-lower alkoxy, carboxyl, carbamoyl, N-lower alkylcarbamoyl, N,N-di-lower alkylcarbamoyl or nitrile; $R_2$ and $R_4$ simultaneously or independently of one another are hydrogen, unsubstituted or substituted lower alkanoyl or aroyl, or a radical which can be removed under physiological conditions, e.g. a protective group;
  $R_3$ is hydrogen, lower alkyl, hydroxy-lower alkyl, halo-lower alkyl, carboxy-lower alkyl, lower alkoxycarbonyl-lower alkyl, $R_6R_7N$—C(O)-lower alkyl, unsubstituted or substituted aryl or aryl-lower alkyl, or unsubstituted or substituted heteroaryl or heteroaralkyl; $R_6$ and $R_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl) amino-lower alkyl, N,N-di(hydroxy-lower alkyl) amino-lower alkyl or, together with the nitrogen atom to which they are bonded, form an azaalicyclic ring; and salts thereof; in the treatment of diseases which cause an excess of metal in the human or animal body or are caused by it; preferably in the form of pharmaceutically acceptable preparations, in particular in a method for the therapeutic treatment of the human body, and to a treatment method of this type.

Halogen is, e.g., chlorine, bromine or fluorine, but can also be iodine.

The prefix "lower" designates a radical having not more than 7 and in particular not more than 4 carbon atoms.

Alkyl is straight-chain or branched. Per se, e.g. lower alkyl, or as a constituent of other groups, e.g. lower alkoxy, lower alkylamine, lower alkanoyl, lower alkylaminocarbonyl, it can be unsubstituted or substituted, e.g. by halogen, hydroxyl, lower alkoxy, trifluoromethyl, cyclo-lower alkyl, azaalicyclyl or phenyl, it is preferably unsubstituted or substituted by hydroxyl.

Lower alkyl is, e.g., n-propyl, isopropyl, n-butyl, isobutyl, sec-butyl, tert-butyl, n-pentyl, neopentyl, n-hexyl or n-heptyl, preferably methyl, ethyl and n-propyl. Halo-lower alkyl is lower alkyl substituted by halogen, preferably chlorine or fluorine, in particular by up to,three chlorine or fluorine atoms.

Lower alkoxy is, e.g., n-propoxy, isopropoxy, n-butoxy, isobutoxy, sec-butoxy, tert-butoxy, n-amyloxy, isoamyloxy, preferably methoxy and ethoxy. Halo-lower alkoxy is lower alkoxy substituted by halogen, preferably chlorine or fluorine, in particular by up to three chlorine or fluorine atoms.

Carbamoyl is the radical $H_2N—C(O)—$, N-lower alkylcarbamoyl is lower alkyl-HN—C(O)— and N,N-di-lower alkylcarbamoyl is di-lower alkyl-N—C(O)—.

Lower alkanoyl is HC(O)— and lower alkyl-C(O)— and is, e.g., acetyl, propanoyl, butanoyl or pivaloyl.

Lower alkoxycarbonyl designates the radical lower alkyl-O—C(O)— and is, e.g., n-propoxycarbonyl, isopropoxycarbonyl, n-butoxycarbonyl, isobutoxycarbonyl, sec-butoxycarbonyl, tert-butoxycarbonyl, n-amyloxycarbonyl, isoamyloxycarbonyl, preferably methoxycarbonyl and ethoxycarbonyl.

Aryl, per se, e.g. aryl, or as a constituent of other groups, e.g. aryl-lower alkyl or aroyl, is, e.g., phenyl or naphthyl, which is substituted or unsubstituted. Aryl is preferably phenyl which is unsubstituted or substituted by one or more, in particular one or two, substituents, e.g. lower alkyl, lower alkoxy, hydroxyl, nitro, halogen, trifluoromethyl, carboxyl, lower alkoxycarbonyl, amino, N-lower alkylamino, N,N-di-lower alkylamino, aminocarbonyl, lower alkylaminocarbonyl, di-lower alkylaminocarbonyl, heterocycloalkyl, heteroaryl or cyano. Primarily, aryl is unsubstituted phenyl or naphthyl, or phenyl which is substituted by lower alkyl, lower alkoxy, hydroxyl, halogen, carboxyl, lower alkoxycarbonyl, N,N-di-lower alkylamino or heterocycloalkylcarbonyl.

Aroyl is the radical aryl-C(O)— and is, e.g., benzoyl, toluoyl, naphthoyl or p-methoxybenzoyl.

Aryl-lower alkyl is, e.g., benzyl, p-chlorobenzyl, o-fluorobenzyl, phenylethyl, p-tolylmethyl, p-dimethylaminobenzyl, p-diethylaminobenzyl, p-cyanobenzyl, p-pyrrolidinobenzyl.

Heterocycloalkyl designates a cycloalkyl radical having 3 to 8, in particular having from 5 to not more than 7, ring atoms, of which at least one is a heteroatom; oxygen, nitrogen and sulfur are preferred. Azaalicyclyl is a saturated cycloalkyl radical having 3–8, in particular 5–7, ring atoms, in which at least one of the ring atoms is a nitrogen atom. Azaalicyclyl can also contain further ring heteroatoms, e.g. oxygen, nitrogen or sulfur; it is, e.g., piperidinyl, piperazinyl, morpholinyl or pyrrolidinyl. Azaalicyclyl radicals can be unsubstituted or substituted by halogen or lower alkyl. The azaalicyclyl radicals bonded via a ring nitrogen atom, which are preferred, are, as is known, designated as piperidino, piperazino, morpholino, pyrrolidino etc.

Heteroaryl per se, e.g. heteroaryl, or as a constituent of other substituents, e.g. heteroaryl-lower alkyl, is an aromatic radical having from 3 to not more than 7, in particular from 5 to not more than 7, ring atoms, in which at least one of the ring atoms is a heteroatom, e.g. pyrrolyl, imidazolyl, triazolyl, tetrazolyl, oxazolyl, thiazolyl, furanyl, thiophenyl, pyridyl, pyrazinyl, oxazinyl, thiazinyl, pyranyl or pyrimidinyl. Heteroaryl can be substituted or unsubstituted. Heteroaryl which is unsubstituted or substituted by one or more, in particular one or two, substituents, e.g. lower alkyl, halogen, trifluoromethyl, carboxyl or lower alkoxycarbonyl, is preferred.

Heteroaryl-lower alkyl designates a lower alkyl radical in which at least one of the hydrogen atoms, preferably on the terminal C atom, is replaced by a heteroaryl group if the alkyl chain contains two or more carbon atoms.

N-lower alkylamino is, e.g., n-propylamino, n-butylamino, i-propylamino, i-butylamino, hydroxyethylamino, preferably methylamino and ethylamino. In N,N-di-lower alkylamino, the alkyl substituents can be identical or different. Thus N,N-di-lower alkylamino is, e.g., N,N-dimethylamino, N,N-diethylamino, N,N-methylethylamino, N-methyl-N-morpholinoethylamino, N-methyl-N-hydroxyethylamino or N-methyl-N-benzylamino.

Salts of compounds of the formula I are, in particular, pharmaceutically acceptable salts, especially salts with bases, such as appropriate alkali metal or alkaline earth metal salts, e.g. sodium, potassium or magnesium salts, pharmaceutically acceptable transition metal salts such as zinc salts, or salts with organic amines, such as cyclic amines, such as mono-, di- or tri-lower alkylamines, such as hydroxy-lower alkylamines, e.g. mono-, di- or trihydroxy-lower alkylamines, hydroxy-lower alkyl-lower alkylamines or polyhydroxy-lower alkylamines. Cyclic amines are, e.g., morpholine, thiomorpholine, piperidine or pyrrolidine. Suitable mono-lower alkylamines are, e.g., ethyl- and tert-butylamine; di-lower alkylamines are, e.g., diethyl- and diisopropylamine; and tri-lower alkylamines are, e.g., trimethyl- and triethylamine. Appropriate hydroxy-lower alkylamines are, e.g., mono-, di- and triethanolamine; hydroxy-lower alkyl-lower alkylamines are, e.g., N,N-dimethylamino- and N,N-diethylaminoethanol; a suitable polyhydroxy-lower alkylamine is, e.g., glucosamine. In other cases it is also possible to form acid addition salts, e.g. with strong inorganic acids, such as mineral acids, e.g. sulfuric acid, a phosphoric acid or a hydrohalic acid, with strong organic carboxylic acids, such as lower alkanecarboxylic acids, e.g. acetic acid, such as saturated or unsaturated dicarboxylic acids, e.g. malonic, maleic or fumaric acid, or such as hydroxycarboxylic acids, e.g. tartaric or citric acid, or with sulfonic acids, such as lower alkane- or substituted or unsubstituted benzenesulfonic acids, e.g. methane- or p-toluenesulfonic acid. Compounds of the formula I having an acidic group, e.g. carboxyl, and a basic group, e.g. amino, can also be present in the form of internal salts, i.e. in zwitterionic form, or a part of the molecule can be present as an internal salt, and another part as a normal salt.

In particular, the invention relates to the use of a compound of formula I for the treatment of diseases which cause an excess of iron in the human or animal body or are caused by it, preferably in the form of pharmaceutically acceptable preparations, in particular in a method for the therapeutic treatment of the human body, and to a treatment method of this type.

In addition, the invention relates to novel preparations, comprising at least one compound of the formula I in which $R_1$ and $R_5$ simultaneously or independently of one another are hydrogen, halogen, hydroxyl, lower alkyl, halo-lower alkyl, lower alkoxy, halo-lower alkoxy, carboxyl, carbamoyl, N-lower alkylcarbamoyl, N,N-di-lower alkylcarbamoyl or nitrile; $R_2$ and $R_4$ simultaneously or independently of one another are hydrogen, unsubstituted or substituted lower alkanoyl or aroyl, or a radical which can be removed under physiological conditions, e.g. a protective group;

$R_3$ is hydrogen, lower alkyl, hydroxy-lower alkyl, halo-lower alkyl, carboxy-lower alkyl, lower alkoxycarbonyl-lower alkyl, $R_6R_7N—C(O)$-lower alkyl, unsubstituted or substituted aryl, aryl-lower alkyl, substituted by N-lower alkylamino, N,N-di-lower alkylamino or pyrrolidino, or unsubstituted or substituted heteroaryl or heteroaralkyl; $R_6$ and $R_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl) amino-lower alkyl, N,N-di(hydroxy-lower alkyl) amino-lower alkyl or, together with the nitrogen atom to which they are bonded, form an azaalicyclic ring; and salts thereof; and at least one pharmaceutically acceptable carrier; and to methods for their preparation. These pharmaceutical preparations are those for enteral, in particular oral, and furthermore rectal, administration and those for parenteral administration to warm-blooded animals, especially to man, the pharmacological active ingredient being contained on its own or together with customary pharmaceutical adjuncts. The pharmaceutical preparations contain (in percentages by weight), e.g., from approximately 0.001% to 100%, preferably from approximately 0.1% to approximately 100%, of the active ingredient.

Pharmaceutical preparations for enteral or parenteral administration are, e.g., those in unit dose forms, such as sugar-coated tablets, tablets, dispersible tablets, effervescent tablets, capsules, suspendable powders, suspensions or suppositories, or ampoules. These are prepared in a manner known per se, e.g. by means of conventional pan-coating, mixing, granulation or lyophilization processes. Pharmaceutical preparations for oral administration can thus be obtained by combining the active ingredient with solid carriers, if desired granulating a mixture obtained and processing the mixture or granules, if desired or necessary, after addition of suitable adjuncts to give tablets or sugar-coated tablet cores.

Suitable carriers are, in particular, fillers such as sugars, e.g. lactose, sucrose, mannitol or sorbitol, cellulose preparations and/or calcium phosphates, e.g. tricalcium phosphate or calcium hydrogen phosphate, furthermore binders, such as starch pastes, using, e.g., maize, wheat, rice or potato starch, gelatin, tragacanth, methylcellulose and/or polyvinylpyrrolidone, and, if desired, disintegrants, such as the abovementioned starches, furthermore carboxymethyl starch, crosslinked polyvinylpyrrolidone, agar or alginic acid or a salt thereof, such as sodium alginate. Adjuncts are primarily flow-regulating and lubricating agents, e.g. salicylic acid, talc, stearic acid or salts thereof, such as magnesium or calcium stearate, and/or polyethylene glycol. Sugar-coated tablet cores are provided with suitable, if desired enteric, coatings, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of enteric coatings, solutions of suitable cellulose preparations, such as acetylcellulose phthalate or hydroxypropylmethylcellulose phthalate. Colorants or pigments, e.g. for the identification or the marking of various doses of active ingredient, can be added to the tablets or sugar-coated tablet coatings.

Dispersible tablets are tablets which rapidly disintegrate in a comparatively small amount of liquid, e.g. water, and which, if desired, contain flavorings or substances for masking the taste of the active ingredient. They can advantageously be employed for the oral administration of large individual doses, in which the amount of active ingredient to be administered is so large that on administration as a tablet which is to be swallowed in undivided form or without chewing that it can no longer be conveniently ingested, in particular by children. Further orally administrable pharmaceutical preparations are hard gelatin capsules and also soft, closed capsules of gelatin and a plasticizer, such as glycerol or sorbitol. The hard gelatin capsules can contain the active ingredient in the form of granules, e.g. as a mixture with fillers, such as lactose, binders, such as starches, and/or glidants, such as talc or magnesium stearate, and, if desired, stabilizers. In soft capsules, the active ingredient is preferably dissolved or suspended in suitable liquids, such as fatty oils, liquid paraffin or liquid polyethylene glycols, it also being possible to add stabilizers.

Moreover, suspendable powders, e.g. those which are described as "powder in bottle", abbreviated "PIB", or ready-to-drink suspensions, are suitable for an oral administration form. For this form, the active ingredient is mixed, e.g., with pharmaceutically acceptable surface-active substances, e.g., sodium lauryl sulfate or polysorbate, suspending auxiliaries, e.g. hydroxypropylcellulose, hydroxypropylmethylcellulose or another known from the prior art and previously described, e.g., in "Handbook of Pharmaceutical Ecipients", pH regulators, such as citric or tartaric acid and their salts or a USP buffer and, if desired, fillers, e.g. lactose, and further auxiliaries, and dispensed into suitable vessels, advantageously single-dose bottles or ampoules. Immediately before use, a specific amount of water is added and the suspension is prepared by shaking. Alternatively, the water can also be added even before dispensing.

Rectally administrable pharmaceutical preparations are, e.g., suppositories which consist of a combination of the active ingredient with a suppository base. A suitable suppository base is, e.g., natural or synthetic triglycerides, paraffin hydrocarbons, polyethylene glycols or higher alkanols. Gelatin rectal capsules can also be used which contain a combination of the active ingredient with a base substance. Possible base substances are, e.g., liquid triglycerides, polyethylene glycols or paraffin hydrocarbons.

For parenteral administration, aqueous solutions of an active ingredient in water-soluble form, e.g. of a water-soluble salt, are primarily suitable; furthermore suspensions of the active ingredient, such as appropriate oily injection suspensions, suitable lipophilic solvents or vehicles, such as fatty oils, e.g. sesame oil, or synthetic fatty acid esters, e.g. ethyl oleate or triglycerides, being used, or aqueous injection suspensions which contain viscosity-increasing substances, e.g. sodium carboxymethylcellulose, sorbitol and/or dextran, and, if desired, also stabilizers.

The dosage of the active ingredient can depend on various factors, such as activity and duration of action of the active ingredient, severity of the illness to be treated or its symptoms, manner of administration, warm-blooded animal species, sex, age, weight and/or individual condition of the warm-blooded animal. The doses to be administered daily in the case of oral administration are between 10 and approximately 120 mg/kg, in particular 20 and approximately 80 mg/kg, and for a warm-blooded animal having a body weight of approximately 40 kg, preferably between approximately 400 mg and approximately 4,800 mg, in particular approximately 800 mg to 3,200 mg, which is expediently divided into 2 to 12 individual doses.

Preferably, the invention relates to novel preparations comprising at least one compound of the formula I in which
R$_1$ and R$_5$ simultaneously or independently of one another are hydrogen, halogen, hydroxyl, lower alkyl, halo-lower alkyl, lower alkoxy or halo-lower alkoxy; R$_2$ and R$_4$ simultaneously or independently of one another are hydrogen or a radical which can be removed under physiological conditions, e.g. a protective group; R$_3$ is lower alkyl, hydroxy-lower alkyl, carboxy-lower alkyl, lower alkoxycarbonyl-lower alkyl, R$_6$R$_7$N—C(O)-lower alkyl, substituted aryl, aryl-lower alkyl, substituted by N-lower alkylamino, N,N-di-lower alkylamino or pyrrolidino, or unsubstituted or substituted heteroaryl or heteroaralkyl; R$_6$ and R$_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl) amino-lower alkyl, N,N-di(hydroxy-lower alkyl) amino-lower alkyl or, together with the nitrogen atom to which they are bonded, form an azaalicyclic ring; and salts thereof; and at least one pharmaceutically acceptable carrier, and to methods for their preparation. These pharmaceutical preparations are those for enteral, in particular oral, and furthermore rectal, administration, and those for parenteral administration to warm-blooded animals, especially to man, the pharmacological active ingredient being present on its own or together with customary pharmaceutical adjuncts. The pharmaceutical preparations contain (in percentages by weight), e.g., from approximately 0.001% to 100%, preferably from approximately 0.1% to approximately 50%, of the active ingredient.

The present invention also makes available novel compounds of the general formula II

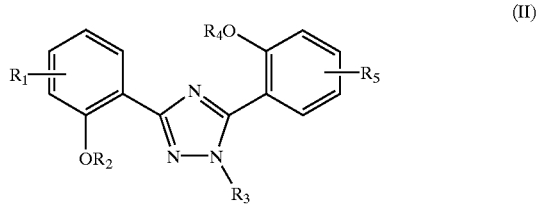

(II)

in which
R$_1$ and R$_5$ simultaneously or independently of one another are hydrogen, halogen, lower-alkyl, halo-lower alkyl, lower alkoxy, halo-lower alkoxy, carboxyl, carbamoyl, N-lower alkylcarbamoyl, N,N-di-lower alkylcarbamoyl or nitrile; R$_2$ and R$_4$ simultaneously or independently of one another are hydrogen, unsubstituted or substituted lower alkanoyl or aroyl, or a radical which can be removed under physiological conditions, e.g. a protective group; R$_3$ is R$_6$R$_7$N—C(O)-lower alkyl, unsubstituted or substituted aryl, aryl-lower alkyl, substituted by N-lower alkylamino, N,N-di-lower alkylamino or pyrrolidino, or unsubstituted or substituted heteroaryl or heteroaralkyl, with the proviso that R$_3$ is not phenyl or phenyl substituted by halogen, nitro, nitrile, hydroxyl, lower alkyl, halo-lower alkyl, lower alkoxy or lower alkoxycarbonyl if R$_2$ and R$_4$ are hydrogen, and R$_1$ and R$_5$ are hydrogen, halogen, lower alkyl, halo-lower alkyl, lower alkoxy or nitrile; R$_6$ and R$_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl) amino-lower alkyl, N,N-di(hydroxy-lower alkyl) amino-lower alkyl or, together with the nitrogen atom to which they are bonded, form an azaalicyclic ring; and salts thereof.

Primarily, the invention relates to compounds of the formula II, in which
R$_1$ and R$_5$ simultaneously or independently of one another are hydrogen, halogen, lower alkyl, halo-lower alkyl, lower alkoxy or halo-lower alkoxy; R$_2$ and R$_4$ simultaneously or independently of one another are hydrogen or a radical which can be removed under physiological conditions, e.g. a protective group; R$_3$ is R$_6$R$_7$N—C(O)-lower alkyl, substituted aryl, aryl-lower alkyl, substituted by N-lower alkylamino, N,N-di-lower alkyl amino or pyrrolidino, or unsubstituted or substituted heteroaralkyl with the proviso that R$_3$ is not phenyl, substituted by halogen, nitro, nitrile, hydroxyl, lower alkyl, halo-lower alkyl, lower alkoxy or lower alkoxycarbonyl, if R$_2$ and R$_4$ are hydrogen and R$_1$ and R$_5$ are hydrogen, halogen, lower alkyl, halo-lower alkyl or lower alkoxy; R$_6$ and R$_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl) amino-lower alkyl, N,N-di(hydroxy-lower alkyl) amino-lower alkyl or, together with the nitrogen atom to which they are bonded, form an azaalicyclic ring; and salts thereof.

In particular, the invention relates to compounds of the formula II, in which
R$_1$ and R$_5$ simultaneously or independently of one another are hydrogen, halogen or lower alkyl;

R$_2$ and R$_4$ are hydrogen; R$_3$ is R$_6$R$_7$N—C(O)-lower alkyl, substituted aryl, substituted by carboxyl or R$_8$R$_9$N—C(O)—, aryl-lower alkyl, substituted by N-lower alkylamino, N,N-di-lower alkylamino or pyrrolidino, or unsubstituted or substituted heteroaralkyl; R$_6$ and R$_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl) amino-lower alkyl or N,N-di(hydroxy-lower alkyl) amino-lower alkyl or, together with the nitrogen atom to which they are bonded, form an azaalicyclic ring; R$_8$ and R$_9$ simultaneously or independently of one another are hydrogen or lower alkyl or, together with the nitrogen atom to which they are bonded, form an azaalicyclic ring; and pharmaceutically acceptable salts thereof.

The invention relates especially to the specific compounds of the formula II and their salts, in particular their pharmaceutically acceptable salts, described in the examples.

The compounds can be prepared in a manner known per se by, e.g., a) reacting a compound of the formula III

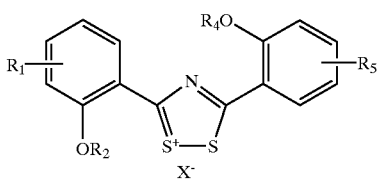
(III)

in which $R_1$, $R_2$, $R_4$ and $R_5$ are as defined above and $X^-$ is an anion, with a compound of the formula IV

$R_3$—NH—NH$_2$ (IV)

in which $R_3$ is as defined above, or a salt thereof; or b) reacting a compound of the formula V

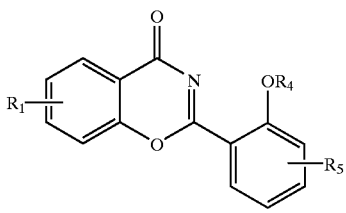
(V)

in which $R_1$, $R_4$ and $R_5$ are as defined above, or a salt thereof, with a compound of the formula IV in which $R_3$ is as defined above, or a salt thereof; or c) reacting a compound of the formula VI

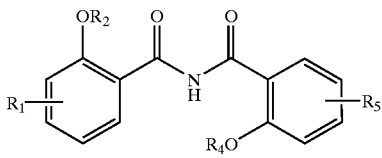
(VI)

in which $R_1$, $R_2$, $R_4$ and $R_5$ are as defined above, with a compound of the formula IV in which $R_3$ is as defined above, or a salt thereof;

and then converting this compound, if necessary, into a compound of the formula II by removal of protective groups, and, if desired, converting it into another compound of the formula II, and/or, if desired, converting a salt obtained into the free compound or into another salt, and/or, if desired, converting a free compound of the formula II obtained and having salt-forming properties into a salt.

In the following more detailed description of the process, the symbols $R_1$–$R_5$ are as defined under the formulae II, III, IV, V and VI, if not stated otherwise.

Process (a): The reaction according to process (a) corresponds to the ring rearrangement reaction of 1,2,4-dithiazolidines to 1,2,4-triazoles, with hydrazines, which is known per se [Wagner et al., Pharmazie 35:48–49 (1980)]. $X^-$ can be any desired anion, preferably a halogen anion, in particular a bromine anion. The reaction can take place with or without solvents, advantageously it is carried out in a polar solvent or solvent mixture, in this case the compound IV can be present as such or alternatively as a solvate, in particular as a hydrate. The reaction proceeds with cooling, at ambient temperature or elevated temperature up to the reflux temperature of the reaction mixture. It is preferably carried out at ambient temperature or elevated temperature.

Process (b): The reaction according to process (b) corresponds to the reaction of benzoxazinones with hydrazines, which is known per se [Wagner et al., Z. Chem. 21:261 (1981) and Ryabukhin et al, Khim. Geterotsiklicheskikh Soed. (3), 406–410 (1983)]. The reaction is carried out in a polar solvent or solvent mixture, preferably in a lower alkanol, in particular methanol or ethanol, if desired with addition of a base, such as a tertiary amine, in particular tri-lower alkylamine, if the compound III and/or IV is present as a salt, e.g. as a hydrohalide. The reaction proceeds with cooling, at ambient temperature or at elevated temperature up to the reflux temperature of the reaction mixture. In a particularly preferred embodiment, the reaction is carried out under reflux in ethanol.

The starting compounds V are accessible, e.g., by the reaction of appropriately substituted salicylic acid with appropriately substituted salicylamide in the presence of thionyl chloride (CH 388252 and Brunetti and Lüthi, Helv. Chim. Acta 55:1566 (1972)]. In addition, the starting compounds V can be prepared by heating a mixture of appropriately substituted salicyloyl chloride with suitably substituted salicylamide.

Process (c): Process (c) corresponds to the reaction of diacylamines with hydrazines, which is known per se [Einhorn et al., Liebigs Ann. Chem. 343:229 (1905), Brunner, Ber. dtsch. chem. Ges. 47:2671 (1914) and Brunner, Mh. Chem. 36:509 (1915)]. The reaction takes place in polar, protic solvents under weak acid catalysis, preferably in aqueous acetic acid at elevated temperature.

The compounds of the formula II can also be prepared according to further processes which are known per se, e.g. according to the processes which are described by Temple, in: The Chemistry of Heterocyclic Compounds, Vol. 37, John Wiley & Sons, New York (1981).

Protective groups, their introduction and removal are described, e.g., in McOmie, Protective Groups in Organic Chemistry, Plenum Press, London, New York (1973), and in Methoden der organischen Chemie [Methods of organic chemistry], Houben-Weyl, 4th Edition, Vol. 1571, Georg Thieme, Stuttgart (1974), and also in Greene, Protective Groups in Organic Synthesis, John Wiley, New York (1981). It is characteristic of protective groups that they can be removed easily, i.e. without undesired side reactions taking place, e.g. solvolytically, reductively, photolytically or alternatively under physiological conditions.

Hydroxyl groups can be present, e.g., in the form of an easily cleavable ester or ether group, preferably of an alkanoyl or aralkanoyl ester group or of a cycloheteroalkyl, aralkyl or alkoxyalkyl ether group, but also of a silyl ester or silyl ether group, in particular as an acetyl or benzoyl ester or as a tetrahydropyranyl, benzyl or methoxymethyl ether.

The starting materials of the formulae III, IV, V and VI are novel in some cases and likewise a subject of the present invention. If necessary, suitable protective groups can be introduced or further derivatization can be carried out according to known methods.

The protective groups which are not a constituent of the desired final product of the formula II are removed in a manner known per se, e.g. by means of solvolysis, in particular hydrolysis, alcoholysis or acidolysis, or by means of reduction, optionally stepwise or simultaneously.

Compounds of the formula II can also be converted into other compounds of the formula II or the formula I.

Thus it is possible to hydrolyze, e.g., a compound of the formula II, in which $R_3$ is an aryl-carboxylic acid ester radical, to the corresponding arylcarboxylic acid, a compound of the formula II being obtained in which $R_3$ is a carboxylic acid radical. The reaction is carried out, e.g., in a polar solvent mixture of a cyclic ether and an alkanol with addition of an alkali metal hydroxide.

When starting compounds of the formula I or any intermediates contain interfering reactive groups, e.g. carboxyl, hydroxyl or amino groups, these can be temporarily protected by easily removable protective groups.

To work up the compounds of the formula II obtainable or their salts and, if necessary, the intermediates, customary processes are used, e.g. solvolysis of excess reagents; recrystallization, chromatography, e.g. partition, ion or gel chromatography, partition between an inorganic and organic solvent phase; single or multiple extraction, in particular after acidification or increasing the basicity or the salt content, drying over hygroscopic salts or at elevated temperature, if desired with passing through or passing by of a gas stream; digestion; filtration; washing; dissolution; evaporation (if necessary in a vacuum or high vacuum); distillation; precipitation; centrifugation; crystallization, e.g. of compounds obtained in oil form or from the mother liquor, it also being possible to seed the final product with a crystal; lyophilization; or a combination of two or more of the working-up steps mentioned, which can also be employed repeatedly; etc.

Starting materials and intermediates can be used in pure form, e.g. after working up, as last-mentioned, in partially purified form or alternatively, e.g., directly as crude products.

The compounds, including their salts, can also be obtained in the form of hydrates or solvates, or their crystals can include, e.g., the solvent used for crystallization.

Solvents and diluents are, e.g., water, alcohols, e.g. lower alkanols, such as methanol, ethanol, propanol, butanol or ethylene glycol monomethyl ether (methylcellosolve), diols, such as ethylene glycol, tri- or polyols, such as glycerol or diethylene glycol, or aryl alcohols, such as phenol or benzyl alcohol, acid amides, e.g. carboxamides, such as N,N-dimethylformamide, or N,N-dimethylacetamide, amides of inorganic acids, such as hexamethylphosphoramide, ethers, e.g. cyclic ethers, such as tetrahydrofuran or dioxane, or acyclic ethers, such as diethyl ether or ethylene glycol dimethyl ether, halogenated hydrocarbons, such as halo-lower alkanes, e.g. methylene chloride or chloroform, ketones, such as acetone, nitrites, such as acetonitrile, esters, such as ethyl acetate, bisalkane sulfoxides, such as dimethyl sulfoxide, nitrogen heterocycles, such as N-methylpyrrolidone or pyridine, hydrocarbons, e.g. lower alkanes, such as hexane or heptane, or aromatics, such as benzene, toluene or xylene(s), or mixtures of these solvents, it being possible for the suitable solvents in each case for the abovementioned reactions and working-up steps to be selected.

In the process of the present invention, those starting substances and intermediates, in each case in free form or in salt form, are preferably used which lead to the compounds II or their salts described as particularly valuable at the outset. Novel starting substances and intermediates, in each case in free form or in salt form, for the preparation of the compounds II or their salts, their use and processes for their preparation also form a subject of the invention.

The invention also relates to those embodiments of the process in which a compound obtainable in any desired process stage as an intermediate is used as a starting material and the missing process steps are carried out, or in which a starting substance is formed under the reaction conditions or is used in the form of a derivative, e.g. of a salt thereof.

Salts of compounds II can be prepared in a manner known per se. Thus acid addition salts, e.g., of compounds II are obtained by treatment with a suitable acid or a suitable ion-exchange reagent and salts with bases are obtained by treatment with a suitable base or a suitable ion-exchange reagent. Salts of compounds of the formula II can be converted in a customary manner into the free compounds II; acid addition salts can be converted, e.g., by treatment with a suitable basic agent or a suitable ion-exchange reagent; and salts with bases can be converted, e.g., by treatment with a suitable acid or a suitable ion-exchange reagent.

Salts of compounds II can be converted into other salts of compounds II in a manner known per se; acid addition salts can be converted, e.g., into other acid addition salts, e.g. by treatment of a salt of an inorganic acid, such as a hydrochloride, with a suitable metal salt, such as a sodium, barium or silver salt, of another acid, e.g. silver acetate, in a suitable solvent, in which an inorganic salt formed, e.g. silver chloride, is insoluble and thus precipitates from the reaction mixture.

Depending on the procedure or reaction conditions, the compounds II with salt-forming properties can be obtained in free form or in the form of salts.

As a result of the close relationship between the compound II in free form and in the form of its salts, in what has been said above and what follows, the free compound II or its salts are, if appropriate, to be understood analogously and expediently as also meaning the corresponding salts or the free compound II.

The compounds II including their salts of salt-forming compounds can also be obtained in the form of their hydrates and/or include other solvents, e.g., if appropriate, solvents used for the crystallization of compounds present in solid form.

The compounds II and their salts, depending on the choice of the starting substances and working procedures, can be present in the form of one of the possible isomers, e.g. stereo-isomers or tautomers, or as a mixture thereof. In this context, pure isomers obtainable are, e.g., pure enantiomers, pure diastereoisomers or pure tautomers. Correspondingly, isomer mixtures which can be present are, e.g., racemates or diastereoisomer mixtures. Isomer mixtures of compounds II in free form or in salt form obtainable according to the process or in other ways can be separated into the components in a customary manner, e.g. on the basis of the physicochemical differences of the constituents, in a known manner by fractional crystallization, distillation and/or chromatography. Advantageously, the more active isomer is isolated.

The following examples are intended to illustrate the invention described above, but without restricting it to them. (Above and below, the following abbreviations—if not stated otherwise—are used: h, hour(s); m.p., melting point; DMSO-$d_6$, hexadeuterodimethyl sulfoxide)

EXAMPLE 1

3,5-Bis(2-hydroxyphenyl)-1-(2-hydroxyethyl)-1H-[1,2,4]triazole 12.0 g of 2-(2-hydroxyphenyl)benz[e][1,3]oxazin-4-one are suspended in 100 ml of methanol and treated with 7.6 g 2-hydroxyethylhydrazine. The mixture is boiled under reflux for 1 h, cooled and 100 ml of water are added. The crystals precipitating in the course of this are filtered off and washed with methanol/water. After drying, the title compound remains as colorless crystals of m.p. 145–147° C.

The starting material can be prepared, e.g., as follows:
a) 2-(2-Hydroxyphenyl)benz[e][1,3]oxazin-4-one 106.0 g of salicyloyl chloride and 93.0 g of salicylamide are mixed and heated at 170° C. for 30 min until hydrogen chloride no longer escapes. The mixture is cooled and the residue is crystallized from ethanol. After drying, 2-(2-hydroxyphenyl)benz[e][1,3]oxazin-4-one is obtained as slightly yellow crystals of m.p. 206–208° C.

EXAMPLE 2

Ethyl [3,5bis(2-hydroxyphenyl)-[1,2,4]triazol-1-yl]acetate 51.5 g of 2-(2-hydroxyphenyl)benz[e][1,3]oxazin-4-one, 30.5 ml of triethylamine and 33.4 g of ethyl hydrazinoacetate hydrochloride are boiled under reflux for 0.5 h in 450 ml of ethanol. On cooling, the product precipitates in crystalline form. It is filtered off and washed with ethanol. After drying, ethyl [3,5-bis(2-hydroxyphenyl)-[1,2,4]triazol-1-yl]acetate remains as colorless crystals of m.p. 172–174° C.

EXAMPLE 3

3,5-Bis(2-hydroxyphenyl)-1-(2,2,2-trifluoroethyl)-1H-[1,2,4]triazole 1.38 g of 2-(2-hydroxyphenyl)benz[e][1,3]oxazin-4-one boiled under reflux for 0.5 h with 1.6 ml of 2,2,2-trifluorethylhydrazine in 20 ml of ethanol. The mixture is cooled, poured onto water and extracted with ethyl acetate. The combined organic phases are dried over sodium sulfate and concentrated on a rotary evaporator. The residue is crystallized from methanol/water. After drying, 3,5-bis(2-hydroxyphenyl)-1-(2,2,2-trifluoroethyl)-1H-[1,2,4]triazole remains as colorless crystals of m.p. 154–156° C.

EXAMPLE 4

3,5-Bis(2-hydroxyphenyl)-1-(4-nitrophenyl)-1 H-[1,2,4]triazole 1.0 g of 2-(2-hydroxyphenyl)benz[e][1,3]oxazin-4-one, 0.5 ml of triethylamine and 0.7 g of 4-nitrophenylhydrazine hydrochloride are boiled under reflux for 1 h in 10 ml of ethanol. On cooling, the product precipitates in crystalline form. It is filtered off and washed with ethanol. After drying, 3,5-bis(2-hydroxyphenyl)-1-(4-nitrophenyl)-1H-[1,2,4]triazole remains as colorless crystals of m.p. 180–183° C.

EXAMPLE 5

4-[3,5-Bis(2-hydroxyphenyl)-[1,2,4]triazol-1-yl]benzoic acid 5.0 g of 2-(2-hydroxyphenyl)benz[e][1,3]oxazin-4-one and 3.5 g of 4-hydrazinobenzoic acid are boiled under reflux for 2 h in 75 ml of ethanol. The crystals precipitating on cooling are washed with ethanol. After drying, 4-[3,5-bis(2-hydroxyphenyl)-[1,2,4]triazol-1-yl]-benzoic acid remains as colorless crystals of m.p. 264–265 C.

EXAMPLE 6

{4-[3,5-Bis(2-hydroxyphenyl)-[1,2,4]triazol-1-yl]-phenyl}morpholin-4-yl-methanone 3.0 g of 4-[3,5-bis(2-hydroxyphenyl)-[1,2,4]triazol-1-yl]benzoic acid (Example 5) and 1.25 ml of 1-chloro-N,N-2-trimethyl-1-propen-1-amine [CAS-Reg.-No. 26189-59-3] are stirred for 2 h in 50 ml of tetrahydrofuran. 2.2 ml of triethylamine and 0.8 ml of morpholine are added and the mixture is stirred at room temperature for 18 h. It is poured onto water and extracted with ethyl acetate. The combined organic phases are dried over sodium sulfate and concentrated on a rotary evaporator. The residue is crystallized from isopropanol. After drying, {4-[3,5-bis(2-hydroxyphenyl)-[1,2,4]triazol-1-yl]-phenyl}morpholin-4-yl-methanone remains as colorless crystals of m.p. 157–160° C.

EXAMPLE 7

{4-[3,5-Bis(2-hydroxyphenyl)-[1,2,4]triazol-1-yl]-phenyl}-(4-methylpiperazin-1-yl)-methanone 3 g of 4-[3,5-bis(2-hydroxyphenyl)-[1,2,4]triazol-1-yl]-benzoic acid (Example 5) and 1.25 ml of 1-chloro-N,N-2-trimethyl-1-propen-1-amine are stirred for 2 h in 50 ml of tetrahydrofuran. 2.2 ml of triethylamine and 1 ml of N-methylpiperazine are added and the mixture is stirred at room temperature for 48 h. It is poured onto water and extracted with ethyl acetate. The combined organic phases are dried over sodium sulfate and concentrated on a rotary evaporator. The residue is crystallized from isopropanol. After drying, {4-[3,5-bis(2-hydroxy-phenyl)-[1,2,4]triazol-1-yl]-phenyl}-(4-methylpiperazin-1-yl)methanone remains as colorless crystals of m.p. 226–229° C.

EXAMPLE 8

3,5-Bis(2-hydroxyphenyl)-1-(4-methoxyphenyl)-1 H-[1,2,4]triazole 5 g of 2-(2-hydroxyphenyl)benz[e][1,3]oxazin-4-one, 3.7 g of 4-methoxyphenylhydrazine hydrochloride and 3 ml of triethylamine are boiled under reflux for 2 h in 75 ml of ethanol. The mixture is cooled, poured onto water and extracted with ethyl acetate. The combined organic phases are dried over sodium sulfate and concentrated on a rotary evaporator. The residue is crystallized from isopropanol. After drying, 3,5-bis(2-hydroxyphenyl)-1-(4-methoxyphenyl)-1H-[1,2,4]triazole remains as colorless crystals of m.p. 179–181° C.

EXAMPLE 9

3,5-Bis(2-hydroxyphenyl)-1-(2,4-difluorophenyl)-1H-[1,2,4]triazole 5.0 g of 2-(2-hydroxyphenyl)benz[e][1,3]oxazin-4-one, 3.9 g of 2,4-difluorophenylhydrazine hydrochloride and 3 ml of triethylamine are boiled under reflux for 2 h in 25 ml of ethanol. The mixture is cooled, poured onto water and extracted with ethyl acetate. The combined organic phases are dried over sodium sulfate and concentrated on a rotary evaporator. The residue is crystallized from ethanol. After drying, 3,5-bis(2-hydroxyphenyl)-1-(2,4-difluoro-phenyl)-1H-[1,2,4]triazole remains as colorless crystals of m.p. 144–146 C.

EXAMPLE 10

3,5-Bis(2-hydroxyphenyl)-1-benzyl-1H-[1,2,4]triazole 5.0 g of 2-(2-hydroxyphenyl)benz[e][1,3]oxazin-4-one are boiled under reflux for 4 h with 3.4 g of benzylhydrazine hydrochloride and 5.9 ml of triethylamine in 50 ml of ethanol. The mixture is cooled, poured onto water and extracted with ethyl acetate. The combined organic phases are dried over sodium sulfate and concentrated on a rotary evaporator. The residue is crystallized from isopropanol. After drying, 3,5-bis(2-hydroxyphenyl)-1-benzyl-1H-[1,2,4]triazole remains as colorless crystals of m.p. 166–168° C.

EXAMPLE 11

4-[3,5Bis(2-hydroxyphenyl)-[1,2,4]triazol-1-ylmethyl]benzonitrile 5.0 g of 2-(2-hydroxyphenyl)benz[e][1,3]oxazin-4-one, 3.9 g of 4-cyanobenzylhydrazine hydrochloride and 6 ml of triethylamine are boiled under reflux for 3 h in 50 ml of ethanol. The mixture is cooled, poured onto water and extracted with ethyl acetate. The combined organic phases are dried over sodium sulfate and concentrated on a rotary evaporator. The residue is crystallized from ethanol/water. After drying, 4-[3,5-bis(2-hydroxyphenyl)-[1,2,4]triazol-1-ylmethyl]benzonitrile remains as colorless crystals of m.p. 147–149° C.

EXAMPLE 12

3,5-Bis(2-hydroxyphenyl)-1-(4-diethylaminobenzyl)-1H-[1,2,4]triazole 5.0 g of 2-(2-hydroxyphenyl)benz[e][1,3]oxazin-4-one are boiled under reflux for 18 h with 5.4 g of 4-diethylaminobenzylhydrazine hydrochloride and 6.7 ml of triethylamine in 50 ml of ethanol. The mixture is poured onto water and extracted with ethyl acetate. The combined organic phases are dried over sodium sulfate and concentrated on a rotary evaporator. The residue is crystallized from isopropanol. After drying, 3,5-bis(2-hydroxyphenyl)-1-(4-diethylaminobenzyl)-1H-[1,2,4]triazole remains as colorless crystals of m.p. 125–127° C.

EXAMPLE 13

3,5-Bis(2-hydroxyphenyl)-1-(4-pyrrolidin-1-yl-benzyl)-1H-[1,2,4]triazole 5.0 g of 2-(2-hydroxyphenyl)benz[e][1,3]oxazin-4-one are boiled under reflux for 18 h with 5.2 g of (4-pyrrolidin-1-yl-benzyl)hydrazine hydrochloride and 6.7 ml of triethylamine in 50 ml of ethanol. The mixture is poured onto water and extracted with ethyl acetate. The combined organic phases are dried over sodium sulfate and concentrated on a rotary evaporator. The residue is crystallized from ethyl acetate/hexane. After drying, 3,5-bis(2-hydroxyphenyl)-1-(4-pyrrolidin-1-ylmethyl)-1H-[1,2,4]triazole remains as colorless crystals of m.p. 153–155° C.

The starting material can be prepared, e.g., as follows:
a) (4-Pyrrolidin-1-yl-benzyl)hydrazine hydrochloride 7.0 g of 4-pyrrolidinobenzaldehyde and 5.3 g of tert-butyl carbazate are boiled under reflux for 5 h in 50 ml of ethanol. The mixture is cooled, diluted with ethanol to 250 ml, 1.0 g of palladium/carbon (10%) is added and the mixture is hydrogenated until 1 mole of hydrogen per mole of starting material has been absorbed. The catalyst is filtered off and the filtrate is concentrated to dryness on a rotary evaporator. The residue is taken up in 90 ml of 4 M hydrogen chloride/dioxane and allowed to stand at room temperature for 20 h. After freeze-drying, (4-pyrrolidin-1-ylbenzyl)-hydrazine hydrochloride is obtained as a yellowish solid. MS: 192 ($M^+$+H)

EXAMPLE 14

3,5-Bis(2-hydroxyphenyl)-1-(pyridin-4-ylmethyl)-1H-[1,2,4]triazole 5.0 g of 2-(2-hydroxyphenyl)benz[e][1,3]oxazin-4-one are boiled under reflux for 4 h with 5.9 g of 4-hydrazinomethylpyridine hydrochloride in [CAS-Reg. No.: 89598-56-1] and 10 ml of triethylamine in 50 ml of ethanol. The mixture is cooled, poured onto water and extracted with ethyl acetate. The combined organic phases are dried over sodium sulfate and concentrated on a rotary evaporator. The residue is crystallized from isopropanol. After drying, 3,5-bis(2-hydroxyphenyl)-1-(pyridin-4-ylmethyl)-1H-[1,2,4]triazole remains as colorless crystals of m.p. 197–199° C.

EXAMPLE 15

3,5-Bis(2-hydroxyphenyl)-1-(pyridin-3-ylmethyl)-1H-[1,2,4]triazole 5.0 g of 2-(2-hydroxyphenyl)benz[e][1,3]oxazin-4-one are boiled under reflux for 5 h with 6.2 g of 3-hydrazinomethylpyridine hydrochloride (57616-01-0) and 13 ml of triethylamine in 50 ml of ethanol. The mixture is cooled, poured onto water and extracted with ethyl acetate. The combined organic phases are dried over sodium sulfate and concentrated on a rotary evaporator. The residue is crystallized from isopropanol. After drying, 3,5-bis(2-hydroxy-phenyl)-1-(pyridin-3-ylmethyl)-1H-[1,2,4]triazole remains as colorless crystals of m.p. 174–176° C.

EXAMPLE 16

3,5-Bis(5-chloro-2-hydroxyphenyl)-1-(2-hydroxyethyl)-1H-[1,2,4]triazole 15.0 g of 6-chloro-2-(5-chloro-2-hydroxyphenyl)benz[e][1,3]oxazin-4-one are boiled under reflux for 2 h with 4 ml of hydroxyethylhydrazine in 50 ml of ethanol. The crystals precipitating on cooling are crystallized from ethanol/water. After drying, 3,5-bis(5-chloro-2-hydroxyphenyl)-1-(2-hydroxyethyl)-1H-[1,2,4]triazole remains as colorless crystals of m.p. 166–170° C.

The starting material can be prepared, e.g., as follows:
a) 6-Chloro-2-(5-chloro-2-hydroxyphenyl)benz[e][1,3]oxazin-4-one 40.0 g of 5-chlorosalicyl-amide and 54.0 g of 5-chlorosalicylic acid are boiled under reflux in 400 ml of xylene after addition of 2.5 ml of pyridine. 38 ml of thionyl chloride are added in the course of 2 h, the mixture is stirred for a further 1 h and the solvent is then distilled off under reduced pressure. The residue is suspended in 200 ml of ethanol, filtered off and washed with ethanol. After drying, 6-chloro-2-(5-chloro-2-hydroxyphenyl)benz[e][1,3]oxazin-4-one is obtained as slightly yellow crystals of m.p. 246–248 C.

EXAMPLE 17

4-[3,5-Bis(5-chloro-2-hydroxyphenyl)-[1,2,4]triazol-1-yl]benzoic acid 3.0 g of 6-chloro-2-(5-chloro-2-hydroxyphenyl)benz[e][1,3]oxazin-4-one and 1.7 g of 4-hydrazinobenzoic acid are boiled under reflux for 2 h in 40 ml of ethanol. The crystals precipitating on cooling are recrystallized from isopropanol. After drying, 4-[3,5-bis(5-chloro-2-hydroxyphenyl)-[1,2,4]triazol-1-yl]benzoic acid remains as colorless crystals of m.p. 275–278 C.

EXAMPLE 18

3,5-Bis(5-chloro-2-hydroxyphenyl)-1-(pyridin-2-ylmethyl)-1H-[1,2,4]triazole 3.0 g of 6-chloro-2-(5-chloro-2-hydroxyphenyl)benz[e][1,3]oxazin-4-one are boiled under reflux for 5 h with 1.7 g of 2-hydrazinomethylpyridine hydrochloride and 3 ml of triethylamine in 50 ml of ethanol. The crystals precipitating on cooling are washed with ethanol. After drying, 3,5-bis (5-chloro-2-hydroxyphenyl)-1-(pyridin-2-ylmethyl)-1H-[1,2,4]triazole remains as colorless crystals of m.p. 227–229 C.

EXAMPLE 19

3,5-Bis(5-chloro-2-hydroxyphenyl)-1-(4-dimethylaminobenzyl)-1H-[1,2,4]triazole 3.0 g of 6-chloro-2-(5-chloro-2-hydroxyphenyl)benz[e][1,3]oxazin-4-one are boiled under reflux for 4 h with 2.2 g of 4-dimethylaminobenzylhydrazine hydrochloride and 3 ml of triethylamine in 50 ml of ethanol. The crystals precipitating on cooling are washed with ethanol. After drying, 3,5-bis(5-chloro-2-hydroxyphenyl)-1-(4-dimethylaminobenzyl)-1H-[1,2,4]triazole remains as colorless crystals of m.p. 205–207 C.

EXAMPLE 20

4-[3,5-Bis(5-fluoro-2-hydroxyphenyl)-[1,2,4]triazol-1-yl]-benzoic acid 2.5 g of 6-fluoro-2-(5-fluoro-2-hydroxyphenyl)benz[e][1,3]oxazin-4-one and 1.6 g of 4-hydrazinobenzoic acid are boiled under reflux for 3 h in 25 ml of ethanol. The mixture is cooled, poured onto water and extracted with ethyl acetate. The combined organic phases are dried over sodium sulfate and concentrated on a rotary evaporator. The residue is crytallized from ethyl acetate/hexane. After drying, 4-[3,5-bis(5-fluoro-2-hydroxyphenyl)-[1,2,4]triazol-1-yl]-benzoic acid remains as colorless crystals of m.p. 252–255 C.

The starting material can be prepared, e.g., as follows:
a) 6-Fluoro-2-(5-fluoro-2-hydroxyphenyl)benz[e][1,3]oxazin-4-one
4.3 g of 5-fluoro-salicylamide and 4.7 g of 5-fluorosalicylic acid are boiled under reflux in 50 ml of xylene after addition of 0.3 ml of pyridine. 4.4 ml of thionyl chloride are added in the course of 2 h, the mixture is stirred for a further 1 h and the solvent is then distilled off under reduced pressure. The residue is suspended in 30 ml of ethanol, filtered off and washed with ethanol. After drying, 6-fluoro-2-(5-fluoro-2-hydroxyphenyl)benz[e][1,3]oxazin-4-one is obtained as slightly yellow crystals of m.p. 250–252 C.

EXAMPLE 21

4-[3,5-Bis(2-hydroxy-5-methylphenyl)-[1,2,4]triazol-1-yl]benzoic acid 1.15 g of 2-(6-hydroxy-m-tolyl)-6-methyl-4H-[1,3]benzoxazin-4-one in [CAS-Reg.-No.:24798-7] and 0.6 g of 4-hydrazinobenzoic acid are boiled under reflux for 2 h in 15 ml of ethanol. The crystals precipitating on cooling are crystallized from isopropanol. After drying, 4-[3,5-bis(2-hydroxy-5-methylphenyl)-[1,2,4]triazol-1-yl]benzoic acid remains as colorless crystals of m.p. 268–269° C.

EXAMPLE 22

[3,5-Bis(2-hydroxyphenyl)-[1,2,4]triazol-1-yl]acetic acid 0.6 g of ethyl [3,5-bis(2-hydroxyphenyl)-[1,2,4]triazol-1-yl]acetate (Example 2) is dissolved in 20 ml of methanol with 0.4 g of sodium hydroxide and the mixture is stirred at room temperature for 2 h. It is acidified with 0.1 N hydrochloric acid and the precipitated crystals are filtered off. After washing with water and drying, [3,5-bis(2-hydroxyphenyl)-[1,2,4]triazol-1-yl]acetic acid remains as colorless crystals of m.p. 231–233° C.

EXAMPLE 23

2-[3,5bis(2-hydroxyphenyl)-[1,2,4]triazol-1-yl]-N-methylacetamide 2.0 g of ethyl [3,5-bis(2-hydroxyphenyl)-[1,2,4]triazol-1-yl]acetate (Example 2) are dissolved in 15 ml of ethanol and treated with 0.8 ml of 8M methylamine in ethanol. The mixture is stirred at 60° C. for 3 h and then cooled. The crystals precipitating in the course of this are filtered off and washed with ethanol. After drying, 2-[3,5-bis(2-hydroxyphenyl)-[1,2,4]triazol-1-yl]-N-methylacetamide remains as colorless crystals m.p. 247–249° C.

EXAMPLE 24

2-[3,5-bis(2-hydroxyphenyl)-[1,2,4]triazol-1-yl]-N-(2-hydroxyethyl)acetamide 2.0 g of ethyl [3,5-bis(2-hydroxyphenyl)-[1,2,4]triazol-1-yl]acetate (Example 2) are dissolved in 10 ml of ethanolamine and stirred at room temperature for 2 h. The mixture is concentrated to dryness in vacuo and the residue is crystallized from isopropanol. After drying, 2-[3,5-bis(2-hydroxyphenyl)-[1,2,4]triazol-1-yl]-N-(2-hydroxyethyl)acetamide remains as colorless crystals of m.p. 208–211° C.

EXAMPLE 25

2-[3,5-Bis(2-hydroxyphenyl)-[1,2,4]triazol-1-yl]-N-(2-methoxyethyl)acetamide 4.0 g of ethyl [3,5-bis(2-hydroxyphenyl)-[1,2,4]triazol-1-yl]acetate (Example 2) are dissolved in 30 ml of 2-methoxyethylamine and the mixture is stirred at room temperature for 2 h. It is concentrated to dryness in vacuo and the residue is crystallized from isopropanol. After drying, 2-[3,5-Bis(2-hydroxyphenyl)-[1,2,4]triazol-1-yl]-N-(2-methoxyethyl)acetamide remains as colorless crystals of m.p. 184–186° C.

EXAMPLE 26

2-[3,5-Bis(2-hydroxyphenyl)-[1,2,4]triazol-1-yl]-N-(2,3-dihydroxypropyl)-acetamide 2.0 g of ethyl [3,5-bis(2-hydroxyphenyl)-[1,2,4]triazol-1-yl]acetate (Example 2) and 2.4 g of (+/−) 3-amino-1,2-propanediol are heated at 60° C. for 2 h in 10 ml of ethanol. The crystals precipitating on cooling are filtered off and washed with ethanol. After drying, 2-[3,5-bis(2-hydroxyphenyl)-[1,2,4]triazol-1-yl]-N-(2,3-dihydroxypropyl)acetamide remains as colorless crystals of m.p. 180–181° C.

EXAMPLE 27

2-[3,5-Bis(2-hydroxyphenyl)-[1,2,4]triazol-1-yl]-N-(2-morpholin-4-yl-ethyl)-acetamide 5.0 g of ethyl [3,5-bis(2-hydroxyphenyl)-[1,2,4]triazol-1-yl]acetate (Example 2) and 2.9 ml of 4-(2-aminoethyl)morpholine are boiled under reflux for 18 h in 50 ml of tetrahydrofuran. The mixture is cooled, poured onto water and extracted with ethyl acetate. The combined organic phases are dried over sodium sulfate and concentrated on a rotary evaporator. The residue is crystallized from isopropanol. After drying, 2-[3,5-bis(2-hydroxyphenyl)-[1,2,4]triazol-1-yl]-N-(2-morpholin-4-yl-ethyl)acetamide remains as colorless crystals of m.p. 180–182° C.

EXAMPLE 28

2-[3,5-Bis(2-hydroxyphenyl)-[1,2,4]triazol-1-yl]-N-(2-hydroxyethyl)-N-methyl-acetamide 2.0 g of ethyl [3,5-bis(2-hydroxyphenyl)-[1,2,4]triazol-1-yl]acetate (Example 2) and 8 ml of methylethanolamine are heated at 60° C. for 1 h. The mixture is cooled, poured onto water and extracted with ethyl acetate. The combined organic phases are dried over sodium sulfate and concentrated on a rotary evaporator. The residue is crystallized from isopropanol. After drying, 2-[3,5-bis(2-hydroxyphenyl)-[1,2,4]triazol-1-yl]-N-(2-hydroxy-ethyl)-N-methylacetamide remains as colorless crystals of m.p. 101–104° C.

EXAMPLE 29

2-[3,5-Bis(2-hydroxyphenyl)-[1,2,4]triazol-1-yl]-N-[2-(2-hydroxyethoxy)ethyl[-acetamide 2.0 g of ethyl [3,5-bis(2-hydroxyphenyl)-[1,2,4]triazol-1-yl]acetate (Example 2) and 10 ml of aminoethoxy)ethanol are stirred at room temperature for 2 h. The mixture is poured onto water and extracted with ethyl acetate. The combined organic phases are dried over sodium sulfate and concentrated on a rotary evaporator. The residue is crystallized from isopropanol. After drying, 2-[3,5-bis(2-hydroxyphenyl)-[1,2,4]triazol-1-yl]-N-[2-(2-hydroxyethoxy)ethyl]acetamide remains as colorless crystals of m.p. 173–174° C.

EXAMPLE 30

N-{2-[Bis(2-hydroxyethyl)amino]ethyl}-2-[3,5-bis(2-hydroxyphenyl)-[1,2,4]triazol-1-yl]acetamide 2.0 g of ethyl [3,5-bis(2-hydroxyphenyl)-[1,2,4]triazol-1-yl]acetate (Example 2) and 1.0 g of bis(2-hydroxyethyl)ethylenediamine are boiled under reflux for 24 h in 8 ml of ethanol. The mixture is cooled, poured onto water and extracted with ethyl acetate. The combined organic phases are dried over sodium sulfate and concentrated on a rotary evaporator. The residue is chromatographed on silica gel. After concentration and drying, N-{2-[bis(2-hydroxyethyl)amino]ethyl}-2-[3,5-bis(2-hydroxyphenyl)-[1,2,4]triazol-1-yl]acetamide remains as a colorless foam. $R_f$ value: 0.35 (silica gel 60, methylene chloride/methanol=9/1). $^1$H-NMR (DMSO-$d_6$): 2.5 (m, 6H), 3.1 (m, 2H), 3.4 (m, 4H), 4.2 (bs, 2H), 4.9 (s, 2H), 7.0 (m, 4H), 7.4 (m, 3H), 7.95 (d, 1H), 8.1 (t, 1H), 11.0 ppm (s, 1H).

EXAMPLE 31

2-[3,5-Bis(2-hydroxyphenyl)-(1,2,4]triazol-1-yl]-N-(2-hydroxy-1-hydroxymethyl-ethyl)acetamide 2.0 g of ethyl [3,5-bis(2-hydroxyphenyl)-[1,2,4]triazol-1-yl]acetate (Example 2) and 2.0 g of 2-amino-1,3-propanediol are boiled under reflux for 3 h in 8 ml of ethanol. The crystals precipitating on cooling are recrystallized from isopropanol. After drying, 2-[3,5-bis(2-hydroxyphenyl)-[1,2,4]triazol-1-yl]-N-(2-hydroxy-1-hydroxymethylethyl)acetamide remains as colorless less crystals of m.p. 212–214° C.

EXAMPLE 32

2-[3,5-Bis(2-hydroxyphenyl)-[1,2,4]triazol-1-yl]-N-[2-(4-methylpiperazin-1-yl)-ethyl]acetamide 3 g of ethyl [3,5-bis(2-hydroxyphenyl)-[1,2,4]triazol-1-yl]acetate (Example 2) and 2.5 g of 2-(4-methylpiperazin-1-yl)ethylamine are boiled under reflux for 20 h in 40 ml of ethanol. The mixture is cooled, poured onto water and extracted with ethyl acetate. The combined organic phases are dried over sodium sulfate and concentrated on a rotary evaporator. The residue is chromatographed on silica gel. After concentration and drying, 2-[3,5-bis(2-hydroxyphenyl)-[1,2,4]triazol-1-yl]-N-[2-(4-methylpiperazin-1-yl)ethyl]acetamide is obtained as a colorless foam. $R_f$ value: 0.17 (silica gel 60, methylene chloride/methanol=9/1). $^1$H-NMR (DMSO-$d_6$): 2.1 (s, 3H), 2.3 (m, 10H), 3.15 (m, 2H), 4.9 (s, 2H), 7.0 (m, 4H), 7.4 (m, 3H), 8.0 (m,2H), 11.0 ppm (s, 1H).

EXAMPLE 33

2-[3,5-Bis(2-hydroxyphenyl)-[1,2,4]triazol-1-yl]-N,N-dimethylacetamide 2.0 g of ethyl [3,5-bis(2-hydroxyphenyl)-[1,2,4]triazol-1-yl]acetate (Example 2) are dissolved in 15 ml of ethanolic dimethylamine (33 per cent) and the solution is stirred at 60° C. for 20 h. The crystals precipitating on cooling are recrystallized from isopropanol. After drying, 2-[3,5-bis(2-hydroxyphenyl)-[1,2,4]triazol-1-yl]-N,N-dimethylacetamide remains as colorless crystals of m.p. 196–197° C.

EXAMPLE 34

2-[3,5-Bis(2-hydroxyphenyl)-[1,2,4]triazol-1-yl]-1-morpholin-4-ylethanone 2.0 g of ethyl [3,5-bis(2-hydroxyphenyl)-[1,2,4]triazol-1-yl]acetate (Example 2) and 8 ml of morpholine are boiled under reflux for 1 h. The mixture is cooled, poured onto water and extracted with ethyl acetate. The combined organic phases are dried over sodium sulfate and concentrated on a rotary evaporator. The residue is crystallized from ethyl acetate/-hexane. After drying, 2-[3,5-bis(2-hydroxyphenyl)-[1,2,4]triazol-1-yl]-1-morpholin-4-ylethanone remains as colorless crystals of m.p. 149–151° C.

EXAMPLE 35

2-[3,5-Bis(2-hydroxyphenyl)-[1,2,4]triazol-1-yl]-1-(4-methylpiperazin-1-yl)-ethanone 2.0 g of ethyl [3,5-bis(2-hydroxyphenyl)-[1,2,4]triazol-1-yl]acetate (Example 2) and 8 ml of 1-methylpiperazine are stirred at 80° C. for 3 h. The mixture is cooled, poured onto water and extracted with ethyl acetate. The combined organic phases are dried over sodium sulfate and concentrated on a rotary evaporator. The residue is crystallized from ethanol. After drying, N-benzyl-2-[3,5-bis(2-hydroxyphenyl)-[1,2,4]triazol-1-yl]-1-(4-methylpiperazin-1-yl)ethanone remains as colorless crystals of m.p. 199–201° C.

EXAMPLE 36

N-Benzyl-2-[3,5-bis(2-hydroxyphenyl)-[1,2,4]triazol-1-yl]-N-methylacetamide 2.0 g of ethyl [3,5-bis(2-hydroxyphenyl)-[1,2,4]triazol-1-yl]acetate (Example 2) and 9 ml of N-methylbenzylamine are stirred at 80° C. for 16 h. The mixture is cooled, poured onto water and extracted with ethyl acetate. The combined organic phases are dried over sodium sulfate and concentrated on a rotary evaporator. The residue is crystallized from ethanol/water. After drying, N-benzyl-2-[3,5-bis(2-hydroxyphenyl)-[1,2,4]triazol-1-yl]-N-methylacetamide remains as colorless crystals of m.p. 179–180° C.

EXAMPLE 37

2-[3,5-Bis(2-hydroxyphenyl)-[1,2,4]triazol-1-yl]-N,N-bis(2-hydroxyethyl)-acetamide 2.0 g of ethyl [3,5-bis(2-hydroxyphenyl)-[1,2,4]triazol-1-yl]acetate (Example 2) and 6.5 g of diethanolamine are boiled under reflux for 2 h in 5 ml of ethanol. The mixture is cooled, poured onto water and extracted with ethyl acetate. The combined organic phases are dried over sodium sulfate and concentrated on a rotary evaporator. The residue is chromatographed on silica gel. After concentration and drying, 2-[3,5-bis(2-hydroxyphenyl)-[1,2,4]triazol-1-yl]-N,N-bis(2-hydroxyethyl)acetamide is obtained as a colorless foam. $R_f$ value: 0.28 (silica gel 60, methylene chloride/methanol=9/1). $^1$H-NMR (DMSO-$d_6$): 3,2–3,6 (m, 8H) 4.4–5.1 (b, 2H), 5.35 (s, 2H), 7.0 (m, 4H), 7.4 (m. 3H), 7.95 (d, 1H), 10.4 (bs, 1H), 11.05 ppm (s, 1H).

EXAMPLE 38

2-[3,5-Bis(2-hydroxyphenyl)-[1,2,4]triazol-1-yl]-N-(2-dimethylaminoethyl)-N-methylacetamide 2.0 g of ethyl (3,5-bis(2-hydroxyphenyl)-[1,2,4]triazol-1-yl]acetate (Example 2) and 9 ml of N,N,N'-trimethylethylenediamine are stirred at 80° C. for 5 h. The mixture is cooled, poured onto water and extracted with ethyl acetate. The combined organic phases are dried over sodium sulfate and concentrated on a rotary evaporator. The residue is crystallized from isopropanol. After drying, 2-[3,5-bis(2-hydroxyphenyl)-[1,2,4]triazol-1-yl]-N-(2-dimethylaminoethyl)-N-methylacetamide remains as colorless crystals of m.p. 172–174° C.

EXAMPLE 39

2-[3,5Bis(5-chloro-2-hydroxyphenyl)-[1,2,4]triazol-1-yl]-N-(2-morpholin-4-ethyl)acetamide 4 g of ethyl [3,5-bis(5-chloro-2-hydroxyphenyl)-[1,2,4]triazol-1-yl]acetate (Example 40) and 2.6 g of 4-(2-aminoethyl)morpholine are boiled under reflux for 18 h in 50 ml of ethanol. The mixture is cooled, poured onto water and extracted with ethyl acetate. The combined organic phases are dried over sodium sulfate and concentrated on a rotary evaporator. The residue is crystallized from isopropanol. After drying, 2-[3,5-bis(5-chloro-2-hydroxyphenyl)-[1,2,4]triazol-1-yl]-N-(2-morpholin-4-yl-ethyl)acetamide remains as colorless crystals of m.p. 224–226° C.

EXAMPLE 40

Ethyl [3,5bis(5-chloro-2-hydroxyphenyl)-[1,2,4]triazol-1-yl]acetate 6.0 g of chloro-2-(5-chloro-2-hydroxyphenyl)benz[e][1,3]oxazin-4-one (Example 16), 3.0 triethylamine and 3.3 g of ethyl hydrazinoacetate hydrochloride are boiled under reflux for 2 h in 60 ml of ethanol. On cooling, the product precipitates in crystalline form. It is filtered off and washed with ethanol. After drying, ethyl [3,5-bis(5-chloro-2-hydroxyphenyl)-[1,2,4]triazol-1-yl]acetate is obtained as colorless crystals of m.p. 195–200° C.

EXAMPLE 41

2-[3,5-Bis(2-hydroxyphenyl)-[1,2,4]triazol-1-yl] benzoic acid 4.8 g of 2-(2-hydroxyphenyl)benz[e][1,3]oxazin-4-one and 3.5 g of 2-hydrazinobenzoic acid are boiled under reflux for 4 h in 10 ml of ethanol. The mixture is cooled, poured onto water and extracted with ethyl acetate. The combined organic phases are dried over sodium sulfate and concentrated on a rotary evaporator. The residue is crystallized from ethyl acetate/hexane. After drying, 2-[3,5-bis(2-hydroxyphenyl)-[1,2,4]triazol-1-yl]benzoic acid is obtained as colorless crystals of m.p. 132–138° C.

EXAMPLE 42

Ethyl 4-[3,5-bis(2-hydroxyphenyl)-[1,2,4]triazol-1-yl]benzoate 10 g of 4-[3,5-bis(2-hydroxyphenyl)-[1,2,4]triazol-1-yl] benzoic acid (Example 5) and 0.5 ml of sulfuric acid are boiled under reflux for 20 h in 200 ml of ethanol. The crystals precipitating on cooling are crystallized from isopropanol/water. After drying, ethyl 4-[3,5-bis(2-hydroxyphenyl)-[1,2,4]triazol-1-yl]benzoate is obtained as colorless crystals of m.p. 148–149° C.

Example A to D

Pharmaceutical Preparations

The expression "active ingredient" is below to be understood as meaning a compound of the formula I in free form or in the form of a pharmaceutically acceptable salt, in particular a compound of the type which is described as a product in one of the above examples.

Example A

Tablets, Comprising 200 mg of Active Ingredient Each, can be Prepared as Follows

| Composition (10,000 tablets) | |
|---|---|
| Active ingredient | 2000.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talc and the silica is admixed and the mixture is compressed to give tablets of weight 295.0 mg each and 200 mg active ingredient content, which, if desired, can be provided with breaking notches for finer adjustment of the dosage.

Example B

Coated Tablets, Each Comprising 400 mg of Active Ingredient, can be Prepared as Follows

| Composition (1,000 tablets) | |
|---|---|
| Active ingredient | 400.0 g |
| Lactose | 100.0 g |
| Maize starch | 70.0 g |
| Talc | 8.5 g |
| Calcium stearate | 1.5 g |
| Hydroxypropylmethylcellulose | 2.36 g |
| Shellac | 0.64 g |
| Water | q.s. |
| Dichloromethane | q.s. |

The active ingredient, the lactose and 40 g of the maize starch are mixed and moistened and granulated with a paste prepared from 15 g of maize starch and water (with warming). The granules are dried, and the remainder of the maize starch, the talc and the calcium stearate is added and mixed with the granules. The mixture is compressed to give tablets and these are coated with a solution of hydroxypropylmethylcellulose and shellac in dichloromethane; final weight of the coated tablet: 583 mg.

Example C

Hard Gelatin Capsules, Comprising 500 mg of Active Ingredient, can be Prepared, e.g., in the Following Manner

| Composition (for 1,000 capsules): | |
|---|---|
| Active ingredient | 500.0 g |
| Lactose | 250.0 g |
| Microcrystalline cellulose | 30.0 g |
| Sodium lauryl sulfate | 2.0 g |
| Magnesium stearate | 8.0 g |

The sodium lauryl sulfate is sieved into the lyophilized active ingredient through a sieve having a mesh width of 0.2 mm. Both components are intimately mixed. Then the lactose is first sieved in through a sieve having a mesh width of 0.6 mm and the microcrystalline cellulose is then sieved in through a sieve having a mesh width of 0.9 mm. After that, the ingredients are again intimately mixed for 10 minutes. Finally, the magnesium stearate is sieved in through a sieve having a mesh width of 0.8 mm. After 3 minutes' further mixing, 790 mg each of the formulation obtained are dispensed into hard gelatin capsules of suitable size.

Example D

Oral Suspension Powder, Comprising 300 mg of Active Ingredient, can be Prepared, e.g., as Follows

| Composition (1 administration): | |
|---|---|
| Active ingredient | 300 mg |
| Hydroxypropylcellulose (Klucel HF) | 50 mg |
| Tartaric acid | 100 mg |
| Sodium lauryl sulfate | 100 mg |

The sodium lauryl sulfate is sieved into the lyophilized active ingredient through a sieve having a mesh width of 0.2 mm. Both components are intimately mixed. Then the microcrystalline cellulose is sieved in through a sieve having a mesh width of 0.9 mm. After this, the ingredients are again intimately mixed for 10 minutes. Finally, the tartaric acid is sieved in through a sieve having a mesh width of 0.8 mm. After 3 minutes' further mixing, the mixture is dispensed into a container having a capacity of at least 10 ml. For use, the mixture is made up to 10 ml with water and vigorously shaken.

Compounds of formula I or II and their pharmaceutically acceptable salts have pharmacological activity and are useful as pharmaceuticals as may be demonstrated in animal test methods, e.g. in accordance with the following test methods:

Test I

Iron Excretion Induced by Compounds of Formula I or II [Method as Described in Bergeron et al., J. Med. Chem. 34:2072–2078 (1991)]

Male Sprague-Dawley rats averaging 400 g are housed in Nalgene plastic metabolic cages and are given free access to water. The animals are anesthetized with sodium pentobarbital (50 mg/kg), given ip. The bile duct is cannulated with 22 gauge PE 50 tubing which is inserted ca. 2 cm into the duct and tied firmly in place. A skin-tunneling needle is inserted from the shoulder area around the abdominal incision. The cannula is threaded through the needle until it emerges from the shoulder opening. The cannula is then passed from the animal to the swivel inside a metal torque-transmitting tether, which is attached to a rodent jacket. The cannula is directed from the animal to a Gilson microfraction collector by a fluid swivel mounted above the metabolic cage. This system allows the animal to move freely in the cage while continuous bile samples are being collected. Bile samples are collected in plastic disposable tubes at 3 h intervals for 24 h. Urine,samples are collected in plastic disposable tubes for 24 h.

Compounds of formula I or II are prepared in 60% water, 40% Cremophor RH40 (v/v). All animals are fasted for 48 h before the administration of the compound of formula I or II and the fast is maintained throughout the course of the experiment.

The iron indicator solution, solution A, is prepared by diluting a stock aqueous solution of 0.134 mM mercaptoacetic acid and 1.9 mM bathophenanthrolinedisulfonic acid disodium salt with 5 parts water and 5 parts saturated aqueous sodium acetate. Solution B is prepared as above but without the bathophenanthroline.

An equal volume of a 10% trichloroacetic acid solution in 3 M HCl (solution C) is added to a urine sample (2.5 ml), and the sample heated in a 65° C. bath for 4 h. After filtration through nylon filters, two 1 ml aliquots are removed. Solution A (5 ml) is added to the sample, and solution B (5 ml) is added to the blank. Bile samples are prepared as the urine samples; however, the volumes are reduced. Standard iron curves are generated with each assay. All samples are transferred to polystyrene cuvettes and the absorbance measured at 535 nm.

Compounds of formula I or II are effective in this assay when administered at a dose in the range of from 10 to 200 mg/kg, e.g. 100 to 150 mg/kg. The induced total iron excretion is in the range 10 to 1500 μg Fe/kg body weight, e.g. 90 to 1000 μg Fe/kg body weight.

The following table lists results for representative compounds of formula I or II:

| Compound No. | Dose [mg/kg] | induced total iron excretion [μg Fe/kg body weight] | Compound No. | Dose [mg/kg] | induced total iron excretion [μg Fe/kg body weight] |
|---|---|---|---|---|---|
| 1 | 100 | 368 | 27 | 100 | 451 |
| 2 | 100 | 91 | 28 | 100 | 413 |
| 5 | 100 | 659 | 29 | 100 | 359 |
| 6 | 133 | 968 | 30 | 100 | 447 |
| 17 | 133 | 203 | 31 | 100 | 175 |
| 21 | 120 | 317 | 33 | 100 | 282 |
| 22 | 100 | 147 | 34 | 100 | 204 |
| 24 | 100 | 413 | 35 | 118 | 293 |
| 25 | 100 | 337 | 37 | 100 | 301 |
| 26 | 100 | 171 | 38 | 119 | 970 |

Test II
Iron Excretion Induced by Compounds of Formula I or II [Method as Described in Bergeron et al., Blood 81:2166–2173 (1993)]

Adult (1 to 11 years old) marmosets (*Callithrix jacchus*) of both sexes, weighing 300 to 450 g are kept in pairs at 24–27° C. and a relative humidity of at least 60% in a 12-hour light-dark cycle. The animals are maintained on a pellet diet (No. 962 Nafag, Gossau, Switzerland) supplemented with fruit-vegetable mash, enriched with a vitamin-minerals concentrate (No. 9628 Nafag) and milk. water available ad libitum.

Iron-overloading procedure: The animals are iron-overloaded by 3 i.p. injections of iron (III) hudroxide polyisomaltose (Anaemex, Ciba-Geigy, Basel, Switzerland) at 14-day intervals (200 mg/kg twice and 100 mg/kg at the third injection). Prior to the first exposure to an iron chelator, the marmosets are rested at least 8 weeks.

Chelators administration: The test compounds are dispersed in 40% aqueous Cremophor RH 40 (BASF, Ludwigshafen, Germany) for administration. The applied volume is 5 ml/kg body weight.

Iron excretion studies: The monkeys receive a low-iron diet 7 days before and throughout the experiments (4 days). The diet is prepared by mixing 628.9 g of a liquid diet for primates (Nafag No. 9694), 83 g of the corresponding lipid mixture (Nafag No. 9696), 131.3 g dietary fiber (Sanacell, Nafag) and 1.0 L of distilled water. Each monkey receives 30 g of this liquid diet, mixed with 20 g milk rice per day. The iron content of this food mixture is 3.1 mg per kg. The animals are placed into acrylic glass metabolic cages especially designed for marmosets (square area of 0.2 m$^2$ and 55 cm high), 48 hours prior to drug administration. Marmosets live in pairs or families and react to separation from their mate. To keep the separation stress at a minimum, usually all animals from a family participate in the same experiment. By placing the animals from a social unit into adjacent metabolic cages, the animals, although separated, can see each other. Urine and feces are collected in 24-hour fractions to determine background iron excretion. After p.o. administration of the chelator, the marmosets are maintained in the same metabolic cage for another 48 hours. Urine and feces are collected in 24 hour fractions. Thus, each animal serves as its own control.

Determination of iron excretion: Urinary iron concentration is determined colorimetrically using the bathophenanthroline method [Smith et al., Analyst 77:418-422 (1952)]. Two 100 μl aliquots of each sample are placed into separate wells of a conical-bottom 96-well plate. To each well 100 μl of a 10% trichloroacetic acid solution in 3M HCl are added. After incubation at 65° C. for 4 h, the plate is centrifuged for 10 minutes at 1,300×g. A 100 μl aliquot of each supernatant is transferred into the corresponding well of a flat-bottom 96-well plate. Then, 100 μl of the iron indicator solution (6.32 ml water, 80 μl mercaptoacetic acid, 12.4 mg bathophenanthroline-disulfonic acid disodium salt, 3.16 ml saturated sodium acetate and 4.22 ml NaOH 5.9N) and blank solution (same but without bathophenanthroline) are added to the first and second aliquot of each sample, respectively. The plate is agitated and the absorbance is measured after 30 min at 535 nm with a microplate reader (UVmax, Molecular Devices). The iron concentration of each sample is calculated using a standard curve (0 to 20 μg/ml) after subtraction of the individual blank. Fecal iron in each sample is determined by flame atomic absorption spectrometry after wet-ashing the entire (24-hour) sample of feces. All results are expressed as μg iron excreted per kg body weight. For the calculation of chelator-induced iron excretion, the mean preatment values of each animal are subtracted from the posttreatment values.

Compounds of formula I or II are effective in this assay when administered at a dose in the range of from 10 to 200 mg/kg, e.g. 20 to 150 mg/kg. The induced total iron excretion is in the range of about 10 to 3000 μg Fe/kg body weight, e.g. 20 to 2500 μg Fe/kg body weight.

The following table lists results for representative compounds of formula I or II:

| No. | Dose [mg/kg] | induced iron in urine [μg/kg] | induced iron in feces [μg/k] | No. | Dose [mg/kg] | induced iron in urine [μg/kg] | induced iron in feces [μg/kg] |
|---|---|---|---|---|---|---|---|
| 1 | 89.2 | 35.6 | | 24 | 106.3 | 37.1 | 129.6 |
| 1 | 89.2 | 267.8 | 1701.3 | 24 | 106.3 | 0.1 | 120.8 |
| 1 | 89.2 | 146.5 | 166.3 | 24 | 106.3 | 340.0 | 446.6 |
| 1 | 89.2 | 153.3 | 786.2 | 25 | 110.5 | 24.0 | |
| 1 | 89.2 | 159.4 | 246.2 | 25 | 110.5 | 54.1 | |
| 1 | 89.2 | 254.5 | 818.2 | 25 | 110.5 | 150.8 | 163.2 |
| 5 | 29.9 | 49.3 | 204.8 | 26 | 121.8 | 88.6 | 914.2 |
| 5 | 29.9 | 65.0 | 491.4 | 26 | 121.8 | 78.8 | 0 |
| 5 | 29.9 | 117.5 | 99.0 | 26 | 121.8 | 12.6 | 141.7 |
| 5 | 59.7 | 78.3 | 765.4 | 27 | 127.1 | 74.7 | 470.3 |
| 5 | 59.7 | 72.4 | 611.5 | 27 | 127.1 | 230.9 | 666.9 |
| 5 | 59.7 | 115.2 | 844.6 | 27 | 127.1 | 81.5 | 301.9 |

-continued

| No. | Dose [mg/kg] | induced iron in urine [μg/kg] | induced iron in feces [μg/k] | No. | Dose [mg/kg] | induced iron in urine [μg/kg] | induced iron in feces [μg/kg] |
|---|---|---|---|---|---|---|---|
| 5 | 59.7 | 110.4 | 323.1 | 28 | 111.6 | 18.7 | 408.5 |
| 5 | 59.7 | 118.9 | 324.7 | 28 | 111.6 | 75.6 | 748.2 |
| 5 | 59.7 | 62.8 | 551.7 | 28 | 111.6 | 15.3 | 87.6 |
| 5 | 119.4 | 169.3 | 2187.2 | 29 | 119.5 | 100.7 | 134.6 |
| 5 | 119.4 | 442.2 | 2025.7 | 29 | 119.5 | 45.9 | 200.7 |
| 5 | 119.4 | 92.6 | 709.9 | 29 | 119.5 | 26.8 | 176.7 |
| 5 | 119.4 | 87.3 | 1171.1 | 30 | 132.5 | 44.4 | 583.0 |
| 5 | 119.4 | 67.7 | 782.8 | 30 | 132.5 | 121.8 | 719.4 |
| 6 | 133.2 | 24.5 | 629.6 | 30 | 132.5 | 20.3 | 396.7 |
| 6 | 133.2 | 59.4 | 327.9 | 38 | 118.7 | 163.5 | 4.8 |
| 6 | 133.2 | 84.6 | 1298.2 | 38 | 118.7 | 132.8 | 314.2 |

No: Compound of Example

What is claimed is:

1. A method of treating diseases which cause an excess of metal in a human or animal body or are caused by an excess of metal in a human or animal body comprising administering to a subject in need of such treatment a therapeutically effective amount of a compound of formula I

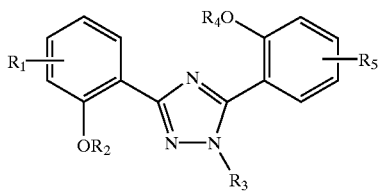

(I)

in which

R$_1$ and R$_5$ simultaneously or independently of one another are hydrogen, halogen, hydroxyl, lower alkyl, halo-lower alkyl, lower alkoxy, halo-lower alkoxy, carboxyl, carbamoyl, N-lower alkylcarbamoyl, N,N-di-lower alkylcarbamoyl or nitrile;

R$_2$ and R$_4$ simultaneously or independently of one another are hydrogen, unsubstituted or substituted lower alkanoyl or aroyl, or a protective group;

R$_3$ is hydrogen, lower alkyl, hydroxy-lower alkyl, halo-lower alkyl, carboxy-lower alkyl, lower alkoxycarbonyl-lower alkyl, R$_6$R$_7$N—C(O)-lower alkyl, unsubstituted or substituted aryl or aryl-lower alkyl, or unsubstituted or substituted heteroaryl or heteroaralkyl;

R$_6$ and R$_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl)amino-lower alkyl, N,N-di(hydroxy-lower alkyl)amino-lower alkyl or, together with the nitrogen atom to which they are bonded, form an azaalicyclic ring;

or a pharmaceutically acceptable salt thereof.

2. The method according to claim 1 wherein the metal is iron.

3. A method of treating diseases which cause an excess of metal in a human or animal body or are caused by an excess of metal in a human or animal body comprising administering to a subject in need of such treatment a therapeutically effective amount of a compound of formula (II)

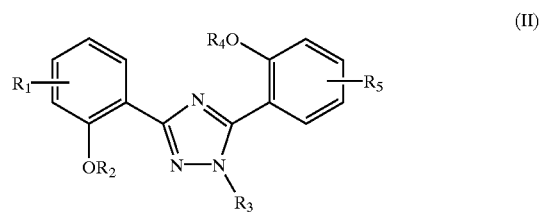

(II)

wherein each of R$_1$ and R$_5$, independently, is hydrogen; halogen; lower alkyl; halo-lower alkyl; lower alkoxy; halo-lower alkoxy; carboxyl; carbamoyl; N-lower alkylcarbamoyl; N,N-di-lower alkylcarbamoyl; or nitrile;

each of R$_2$ and R$_4$, independently, is hydrogen; unsubstituted or substituted lower alkanoyl or aroyl; or a protective group;

R$_3$ is R$_6$R$_7$N—C(O)-lower alkyl; unsubstituted or substituted aryl; aryl-lower alkyl substituted by N-lower alkylamino, N,N-di-lower alkylamino or pyrrolidino; or unsubstituted or substituted heteroaryl or heteroaralkyl, with the proviso that R$_3$ is not phenyl or phenyl substituted by halogen, nitro, nitrile, hydroxyl, lower alkyl, halo-lower alkyl, lower alkoxy or lower alkoxycarbonyl if R$_2$ and R$_4$ are hydrogen, and R$_1$ and R$_5$ are hydrogen, halogen, lower alkyl, halo-lower alkyl, lower alkoxy or nitrile; and each of R$_6$ and R$_7$, independently, is hydrogen; lower alkyl; hydroxy-lower alkyl; alkoxy-lower alkyl; hydroxyalkoxy-lower alkyl; amino-lower alkyl; N-lower alkylamino-lower alkyl; N,N-di-lower alkylamino-lower alkyl; N-(hydroxy-lower alkyl) amino-lower alkyl; N,N-di(hydroxy-lower alkyl) amino-lower alkyl or, together with the nitrogen atom to which they are bonded, form an azaalicyclic ring;

or a pharmaceutically acceptable salt thereof.

4. The method according to claim 3 wherein a compound of formula (II) is administered in each of R$_1$ and R$_5$, independently, is hydrogen; halogen; lower alkyl; halo-lower alkyl; lower alkoxy; or halo-lower alkoxy;

each of R$_2$ and R$_4$, independently, is hydrogen; or a protective group;

R$_3$ is R$_6$R$_7$N—C(O)-lower alkyl; substituted aryl; aryl-lower alkyl substituted by N-lower alkylamino, N,N-di-lower alkyl amino or pyrrolidino; or unsubstituted or substituted heteroaryl or heteroaralkyl with the proviso that R$_3$ is not phenyl or phenyl substituted by halogen, nitro, nitrile, hydroxyl, lower alkyl, halo-lower alkyl, lower alkoxy or lower alkoxycarbonyl if $R_2$ and $R_4$ are hydrogen, and $R_1$ and $R_5$ are hydrogen, halogen, lower alkyl, halo-lower alkyl or lower alkoxy or nitrile; and each of $R_6$ and $R_7$, independently, is hydrogen; lower alkyl; hydroxy-lower alkyl; alkoxy-lower alkyl; hydroxyalkoxy-lower alkyl; amino-lower alkyl; N-lower alkylamino-lower alkyl; N,N-di-lower alkylamino-lower alkyl; N-(hydroxy-lower alkyl) amino-lower alkyl; N,N-di(hydroxy-lower alkyl) amino-lower alkyl or, together with the nitrogen atom to which they are bonded, form an azaalicyclic ring;

or a pharmaceutically acceptable salt thereof.

5. The method according to claim 3 wherein a compound of formula (II) is administered in which each of $R_1$ and $R_5$, independently, is hydrogen; halogen; or lower alkyl;

$R_2$ and $R_4$ are hydrogen;

$R_3$ is $R_6R_7N$—C(O)-lower alkyl; aryl substituted by carboxyl or $R_8R_9N$—C(O)—; aryl-lower alkyl substituted by N-lower alkylamino, N,N-di-lower alkylamino or pyrrolidino; or unsubstituted or substituted heteroaralkyl;

each of $R_6$ and $R_7$, independently, is hydrogen; lower alkyl; hydroxy-lower alkyl; alkoxy-lower alkyl; hydroxyalkoxy-lower alkyl; amino-lower alkyl; N-lower alkylamino-lower alkyl; N,N-di-lower alkylamino-lower alkyl; N-(hydroxy-lower alkyl) amino-lower alkyl; N,N-di(hydroxy-lower alkyl) amino-lower alkyl or, together with the nitrogen atom to which they are bonded, form an azaalicyclic ring;

each of $R_8$ and $R_9$, independently, is hydrogen; lower alkyl or, together with the nitrogen atom to which they are bonded, form an azaalicyclic ring;

or a pharmaceutically acceptable salt thereof.

6. A method of treating diseases which cause an excess of metal in a human or animal body or are caused by an excess of metal in a human or animal body comprising administering to a subject in need of such treatment a therapeutically effective amount of a compound selected from the group consisting of:

{4-[3,5-bis(2-hydroxyphenyl)-[1,2,4]triazol-1-yl]phenyl}-(4-methylpiperazin-1-yl)methanone;

{4-[3,5-bis(2-hydroxyphenyl)-[1,2,4]triazol-1-yl]phenyl}morpholin-4-ylmethanone;

2-[3,5-bis(2-hydroxyphenyl)-[1,2,4]triazol-1-yl]-1-(4-methylpiperazin-1-yl)ethanone;

2-[3,5-bis(2-hydroxyphenyl)-[1,2,4]triazol-1-yl]-1-morpholin-4-yl-ethanone;

2-[3,5-bis(2-hydroxyphenyl)-[1,2,4]triazol-1-yl]-N,N-bis(2-hydroxyethyl)acetamide;

2-[3,5-bis(2-hydroxyphenyl)-[1,2,4]triazol-1-yl]-1-N,N-dimethylacetamide;

2-[3,5-bis(2-hydroxyphenyl)-[1,2,4]triazol-1-yl]-N-(2,3-dihydroxypropyl)acetamide;

2-[3,5-bis(2-hydroxyphenyl)-[1,2,4]triazol-1-yl]-N-(2-dimethylaminoethyl)-N-methylacetamide;

2-[3,5-bis(2-hydroxyphenyl)-[1,2,4]triazol-1-yl]-N-(2-hydroxy-1-hydroxymethylethyl)acetamide;

2-[3,5-bis(2-hydroxyphenyl)-[1,2,4]triazol-1-yl]-N-(2-hydroxyethyl)acetamide;

2-[3,5-bis(2-hydroxyphenyl)-[1,2,4]triazol-1-yl]-N-(2-hydroxyethyl)-N-methylacetamide;

2-[3,5-bis(2-hydroxyphenyl)-[1,2,4]triazol-1-yl]-N-(2-methoxyethyl)acetamide;

2-[3,5-bis(2-hydroxyphenyl)-[1,2,4]triazol-1-yl]-N-(2-morpholin-4-yl-ethyl)acetamide;

2-[3,5-bis(2-hydroxyphenyl)-[1,2,4]triazol-1-yl]-N-[2-(2-hydroxyethoxy)ethyl]acetamide;

2-[3,5-bis(2-hydroxyphenyl)-[1,2,4]triazol-1-yl]-N-[2-(4-methylpiperazin-1-yl)ethyl]acetamide;

2-[3,5-bis(2-hydroxyphenyl)-[1,2,4]triazol-1-yl]-N-methylacetamide;

2-[3,5-bis(5-chloro-2-hydroxyphenyl)-[1,2,4]triazole-1-yl]-N-(2-morpholin-4-yl-ethyl)acetamide;

3,5-bis(2-hydroxyphenyl)-1-(4-diethylaminobenzyl)-1H-[1,2,4]triazole;

3,5-bis(2-hydroxyphenyl)-1-(4-pyrrolidin-1-ylbenzyl)-1H-[1,2,4]triazole;

3,5-bis(2-hydroxyphenyl)-1-(pyridin-3-ylmethyl)-1H-[1,2,4]triazole;

3,5-bis(2-hydroxyphenyl)-1-(pyridin-4-ylmethyl)-1H-[1,2,4]triazole;

3,5-bis(5-chloro-2-hydroxyphenyl)-1-(4-dimethylaminobenzyl)-1H-[1,2,4]triazole;

3,5-bis(5-chloro-2-hydroxyphenyl)-1-(pyridin-2-ylmethyl)-1H-[1,2,4]triazole;

4-[3,5-bis(2-hydroxy-5-methylphenyl)-[1,2,4]triazol-1-yl]benzoic acid;

4-[3,5-bis(2-hydroxyphenyl)-[1,2,4]triazol-1-yl]benzoic acid;

4-[3,5-bis(5-chloro-2-hydroxyphenyl)-[1,2,4]triazol-1-yl]benzoic acid;

4-[3,5-bis(5-fluoro-2-hydroxyphenyl)-[1,2,4]triazol-1-yl]benzoic acid;

N-{2-[bis(2-hydroxyethyl)amino]ethyl}-2-[3,5-bis(2-hydroxyphenyl)-[1,2,4]triazol-1-yl]acetamide; and N-benzyl-2-[3,5-bis(2-hydroxyphenyl)-[1,2,4]triazol-1-yl]-N-methylacetamide;

or a pharmaceutically acceptable salt thereof.

7. The method according to claim 3 wherein the metal is iron.

8. A method of treating iron overload comprising administering a subject in need of such treatment a therapeutically effective amount of a compound of claim 3, or a pharmaceutically acceptable salt thereof.

9. A method of treating diseases which cause an excess of metal in a human or animal body or are caused by an excess of metal in a human or animal body comprising administering to a subject in need of such treatment a therapeutically effective amount of a compound of formula (II)

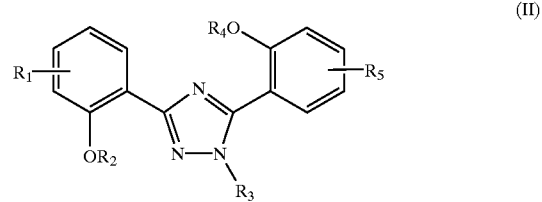

(II)

wherein each of $R_1$ and $R_5$, independently, is hydrogen; halogen; lower alkyl; halo-lower alkyl; lower alkoxy; halo-lower alkoxy; carboxyl; carbamoyl; N-lower alkylcarbamoyl; N,N-di-lower-alkylcarbamoyl; or nitrile;

each of $R_2$ and $R_4$, independently, is hydrogen; unsubstituted lower alkanoyl; lower alkanoyl substituted by halogen, hydroxyl, lower alkoxy, trifluoromethyl, cyclo-lower alkyl or phenyl; unsubstituted aroyl; or aroyl substituted by one or two substituents selected from lower alkyl, lower alkoxy, hydroxyl, nitro, halogen, trifluoromethyl, carboxyl, lower alkoxycarbonyl, amino, N-lower alkylamino, N,N-dilower alkylamino, aminocarbonyl, lower alkylaminocarbonyl, di-lower alkylaminocarbonyl and nitrile;

$R_3$ is $R_6R_7N$—C(O)-lower alkyl; aryl substituted by one or two substituents selected from lower alkyl, lower alkoxy, hydroxyl, nitro, halogen, trifluoromethyl, carboxyl, lower alkoxycarbonyl, amino, N-lower alkylamino, N,N-di-lower alkylamino, aminocarbonyl, lower alkylaminocarbonyl, di-lower alkylaminocarbonyl and nitrile; or aryl-lower alkyl substituted by N-lower alkylamino or N,N-di-lower alkylamino;

with the proviso that $R_3$ is not phenyl substituted by halogen, nitro, nitrile, hydroxyl, lower alkyl, trifluoromethyl, lower alkoxy or lower alkoxycarbonyl if $R_2$ and $R_4$ are hydrogen, and $R_1$ and $R_5$ are hydrogen, halogen, lower alkyl, halo-lower alkyl, lower alkoxy or nitrile; and each of $R_6$ and $R_7$, independently, is hydrogen; lower alkyl; hydroxy-lower alkyl; alkoxy-lower alkyl; hydroxyalkoxy-lower alkyl; amino-lower alkyl; N-lower alkylamino-lower alkyl; N,N-di-lower alkylamino-lower alkyl; N-(hydroxy-lower alkyl)amino-lower alkyl; or N,N-di(hydroxy-lower alkyl)amino-lower alkyl;

or a pharmaceutically acceptable salt thereof.

10. The method of claim 9 wherein a compound of formula (II) is administered in which each of $R_1$ and $R_5$, independently, is hydrogen; halogen; lower alkyl; halo-lower alkyl; lower alkoxy; or halo-lower alkoxy;

each of $R_2$ and $R_4$ is hydrogen;

$R_3$ is $R_6R_7N$—C(O)-lower alkyl; aryl substituted by one or two substituents selected from lower alkyl, lower alkoxy, hydroxyl, nitro, halogen, trifluoromethyl, carboxyl, lower alkoxycarbonyl, amino, N-lower alkylamino, N,N-di-lower alkylamino, aminocarbonyl, lower alkylaminocarbonyl, di-lower alkylaminocarbonyl and nitrile; or aryl-lower alkyl substituted by N-lower alkylamino or N,N-di-lower alkylamino;

with the proviso that $R_3$ is not phenyl substituted by halogen, nitro, nitrile, hydroxyl, lower alkyl, trifluoromethyl, lower alkoxy or lower alkoxycarbonyl if $R_1$ and $R_5$ are hydrogen, halogen, lower alkyl, halo-lower alkyl or lower alkoxy; and each of $R_6$ and $R_7$, independently, is hydrogen; lower alkyl; hydroxy-lower alkyl; alkoxy-lower alkyl; hydroxyalkoxy-lower alkyl; amino-lower alkyl; N-lower alkylamino-lower alkyl; N,N-di-lower alkylamino-lower alkyl; N-(hydroxy-lower alkyl)amino-lower alkyl; or N,N-di(hydroxy-lower alkyl)amino-lower alkyl;

or a pharmaceutically acceptable salt thereof.

11. The method according to claim 9 wherein a compound of formula (II) is administered in which each of $R_1$ and $R_5$, independently, is hydrogen; halogen; or lower alkyl;

each of $R_2$ and $R_4$ is hydrogen;

$R_3$ is $R_6R_7N$—C(O)-lower alkyl; aryl substituted by carboxyl or $R_8R_9N$—C(O)—; or aryl-lower alkyl substituted by N-lower alkylamino or N,N-di-lower alkylamino;

each of $R_6$ and $R_7$, independently, is hydrogen; lower alkyl; hydroxy-lower alkyl; alkoxy-lower alkyl; hydroxyalkoxy-lower alkyl; amino-lower alkyl; N-lower alkylamino-lower alkyl; N,N-di-lower alkylamino-lower alkyl; N-(hydroxy-lower alkyl)amino-lower alkyl; or N,N-di(hydroxy-lower alkyl)amino-lower alkyl; and each of $R_8$ and $R_9$, independently, is hydrogen or lower alkyl;

or a pharmaceutically acceptable salt thereof.

12. The method according to claim 9 wherein the compound which is administered is selected from the group consisting of:

2-[3,5-bis(2-hydroxyphenyl)-[1,2,4]triazol-1-yl]-N,N-bis(2-hydroxyethyl)acetamide;

2-[3,5-bis(2-hydroxyphenyl)-[1,2,4]triazol-1-yl]-N,N-dimethylacetamide;

2-[3,5-bis(2-hydroxyphenyl)-[1,2,4]triazol-1-yl]-N-(2,3-dihydroxypropyl)acetamide;

2-[3,5-bis(2-hydroxyphenyl)-[1,2,4]triazol-1-yl]-N-(2-dimethylaminoethyl)-N-methylacetamide;

2-[3,5-bis(2-hydroxyphenyl)-[1,2,4]triazol-1-yl]-N-(2-hydroxy-1-hydroxymethylethyl)acetamide;

2-[3,5-bis(2-hydroxyphenyl)-[1,2,4]triazol-1-yl]-N-(2-hydroxyethyl)acetamide;

2-[3,5-bis(2-hydroxyphenyl)-[1,2,4]triazol-1-yl]-N-(2-hydroxyethyl)-N-methylacetamide;

2-[3,5-bis(2-hydroxyphenyl)-[1,2,4]triazol-1-yl]-N-(2-methoxyethyl)acetamide;

2-[3,5-bis(2-hydroxyphenyl)-[1,2,4]triazol-1-yl]-N-[2-(2-hydroxyethoxy)ethyl]acetamide;

2-[3,5-bis(2-hydroxyphenyl)-[1,2,4]triazol-1-yl]-N-methylacetamide;

3,5-bis(2-hydroxyphenyl)-1-(4-diethylaminobenzyl)-1H-[1,2,4]triazole;

3,5-bis(5-chloro-2-hydroxyphenyl)-1-(4-dimethylaminobenzyl)-1H-[1,2,4]triazole;

4-[3,5-bis(2-hydroxy-5-methylphenyl)-[1,2,4]triazol-1-yl]benzoic acid;

4-[3,5-bis(2-hydroxyphenyl)-[1,2,4]triazol-1-yl]benzoic acid;

4-[3,5-bis(5-chloro-2-hydroxyphenyl)-[1,2,4]triazol-1-yl]benzoic acid;

4-[3,5-bis(5-fluoro-2-hydroxyphenyl)-[1,2,4]triazol-1-yl]benzoic acid;

N-{2-[bis(2-hydroxyethyl)amino]ethyl}-2-[3,5-bis(2-hydroxyphenyl)-[1,2,4]triazol-1-yl]acetamide; and N-benzyl-2-[3,5-bis(2-hydroxyphenyl)-[1,2,4]triazol-1-yl]-N-methylacetamide;

or a pharmaceutically acceptable salt thereof.

13. The method according to claim 9 wherein the compound which is administered is 4-[3,5-bis(2-hydroxyphenyl)-[1,2,4]triazol-1-yl]benzoic acid, or a pharmaceutically acceptable salt thereof.

14. The method according to claim 9 wherein the compound which is administered is 2-[3,5-bis(2-hydroxyphenyl)-[1,2,4]triazol-1-yl]benzoic acid, or a pharmaceutically acceptable salt thereof.

15. The method according to claim 9 wherein the metal is iron.

16. A method of treating iron overload comprising administering to a subject in need of such treatment a therapeutically effective amount of a compound of formula II, as claimed in claim 9, or a pharmaceutically acceptable salt thereof.

17. The method according to claim 16 wherein the compound which is administered is 4-[3,5-bis(2-hydroxyphenyl)-[1,2,4]triazol-1-yl]benzoic acid, or a pharmaceutically acceptable salt thereof.

18. A method of treating diseases which cause an excess of metal in a human or animal body or are caused by an excess of metal in a human or animal body comprising administering to a subject in need of such treatment a therapeutically effective amount of a compound selected from the group consisting of:

3,5-bis(2-hydroxyphenyl)-1-(2-hydroxyethyl)-1H-[1,2,4]triazole; ethyl[3,5-bis(2-hydroxyphenyl)-[1,2,4]triazol-1-yl]acetate;
3,5-bis(2-hydroxyphenyl)-1-(2,2,2-trifluoroethyl)-1H-[1,2,4]triazole;
3,5-bis(2-hydroxyphenyl)-1-(4-nitrophenyl)-1H-[1,2,4]triazole;
4-[3,5-bis(2-hydroxyphenyl)-[1,2,4]triazol-1-yl]benzoic acid;
{4-[3,5-bis(2-hydroxyphenyl)-[1,2,4]triazol-1-yl]-phenyl}morpholin-4-yl-methanone;
{4-[3,5-bis(2-hydroxyphenyl)-[1,2,4]triazol-1-yl]-phenyl}-(4-methylpiperazin-1-yl)-methanone;
3,5-bis(2-hydroxyphenyl)-1-(4-methoxyphenyl)-1H-[1,2,4]triazole;
3,5-bis(2-hydroxyphenyl)-1-(2,4-difluorophenyl)-1H-[1,2,4]triazole;
3,5-bis(2-hydroxyphenyl)-1-benzyl-1H-[1,2,4]triazole;
4-[3,5-bis(2-hydroxyphenyl)-[1,2,4]triazol-1-ylmethyl]benzonitrile;
3,5-bis(2-hydroxyphenyl)-1-(4-diethylaminobenzyl)-1H-[1,2,4]triazole;
3,5-bis(2-hydroxyphenyl)-1-(4-pyrrolidin-1-ylbenzyl)-1H-[1,2,4]triazole;
3,5-bis(2-hydroxyphenyl)-1-(pyridin-4-ylmethyl)-1H-[1,2,4]triazole;
3,5-bis(2-hydroxyphenyl)-1-(pyridin-3-ylmethyl)-1H-[1,2,4]triazole;
3,5-bis(5-chloro-2-hydroxyphenyl)-1-(2-hydroxyethyl)-1H-[1,2,4]triazole;
4-[3,5-bis(5-chloro-2-hydroxyphenyl)-[1,2,4]triazol-1-yl]benzoic acid;
3,5-bis(5-chloro-2-hydroxyphenyl)-1-(pyridin-2-ylmethyl)-1H-[1,2,4]triazole;
3,5-bis(5-chloro-2-hydroxyphenyl)-1-(4-dimethylaminobenzyl)-1H-[1,2,4]triazole;
4-[3,5-bis(5-fluoro-2-hydroxyphenyl)-[1,2,4]triazol-1-yl]benzoic acid;
4-[3,5-bis(2-hydroxy-5-methylphenyl)-[1,2,4]triazol-1-yl]benzoic acid;
[3,5-bis(2-hydroxyphenyl)-[1,2,4]triazol-1-yl]acetic acid;
2-[3,5-bis(2-hydroxyphenyl)-[1,2,4]triazol-1-yl]-N-methylacetamide;
2-[3,5-bis(2-hydroxyphenyl)-[1,2,4]triazol-1-yl]-N-(2-hydroxyethyl)acetamide;
2-[3,5-bis(2-hydroxyphenyl)-[1,2,4]triazol-1-yl]-N-(2-methoxyethyl)acetamide;
2-[3,5-bis(2-hydroxyphenyl)-[1,2,4]triazol-1-yl]-N-(2,3-dihydroxypropyl)acetamide;
2-[3,5-bis(2-hydroxyphenyl)-[1,2,4]triazol-1-yl]-N-(2-morpholin-4-yl-ethyl)acetamide;
2-[3,5-bis(2-hydroxyphenyl)-[1,2,4]triazol-1-yl]-N-(2-hydroxyethyl)-N-methylacetamide;
2-[3,5-bis(2-hydroxyphenyl)-[1,2,4]triazol-1-yl]-N-[2-(2-hydroxyethoxy)ethyl]-acetamide;
N-{2-[bis(2-hydroxyethyl)amino]ethyl}-2-[3,5-bis(2-hydroxyphenyl)-[1,2,4]triazol-1-yl]acetamide;
2-[3,5-bis(2-hydroxyphenyl)-[1,2,4]triazol-1-yl]-N-[2-hydroxy-1-hydroxymethylethyl)acetamide;
2-[3,5-bis(2-hydroxyphenyl)-[1,2,4]triazol-1-yl]-N-[2-(4-methylpiperazin-1-yl)-ethyl]acetamide;
2-[3,5-bis(2-hydroxyphenyl)-[1,2,4]triazol-1-yl]-N,N-dimethylacetamide;
2-[3,5-bis(2-hydroxyphenyl)-[1,2,4]triazol-1-yl]-1-morpholin-4-ylethanone;
2-[3,5-bis(2-hydroxyphenyl)-[1,2,4]triazol-1-yl]-1-(4-methylpiperazin-1-yl)-ethanone;
N-benzyl-2-[3,5-bis(2-hydroxyphenyl)-[1,2,4]triazol-1-yl]-N-methylacetamide;
2-[3,5-bis(2-hydroxyphenyl)-[1,2,4]triazol-1-yl]-N,N-bis(2-hydroxyethyl)-acetamide;
2-[3,5-bis(2-hydroxyphenyl)-[1,2,4]triazol-1-yl]-N-(2-dimethylaminoethyl)-N-methylacetamide;
2-[3,5-bis(5-chloro-2-hydroxyphenyl)-[1,2,4]triazol-1-yl]-N-(2-morpholin-4-yl-ethyl)acetamide;
ethyl[3,5-bis(5-chloro-2-hydroxyphenyl)-[1,2,4]triazol-1-yl]acetate;
2-[3,5-bis(2-hydroxyphenyl)-[1,2,4]triazol-1-yl]-benzoic acid; and
ethyl-4-(3,5-bis(2-hydroxyphenyl)-[1,2,4]triazol-1-yl]benzoate;
or a pharmaceutically acceptable salt thereof.

* * * * *